(12) United States Patent
Sherr et al.

(10) Patent No.: US 6,482,929 B1
(45) Date of Patent: Nov. 19, 2002

(54) ANTIBODIES TO ARF-P19

(75) Inventors: Charles J. Sherr, Memphis; Dawn E. Quelle, Cordova, both of TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 29 days.

(21) Appl. No.: 09/610,833

(22) Filed: Jul. 6, 2000

Related U.S. Application Data

(62) Division of application No. 09/247,154, filed on Feb. 9, 1999, which is a continuation of application No. 08/954,470, filed on Oct. 20, 1997, now Pat. No. 5,876,965, which is a division of application No. 08/534,975, filed on Sep. 27, 1995, now Pat. No. 5,723,313.

(51) Int. Cl.$^7$ .......................... C07K 16/00; C12P 21/08; G01N 33/536
(52) U.S. Cl. ................ 530/387.9; 530/388.1; 436/512
(58) Field of Search ................ 530/387.9, 388.1; 436/512

(56) References Cited

U.S. PATENT DOCUMENTS

| | | | |
|---|---|---|---|
| 4,965,188 A | 10/1990 | Mullis et al. | 435/6 |
| 5,174,986 A | 12/1992 | Berns | 424/9 |
| 5,185,260 A | 2/1993 | Crissman et al. | 435/244 |
| 5,739,027 A | 4/1998 | Kamb | |

FOREIGN PATENT DOCUMENTS

| | | |
|---|---|---|
| WO | WO 92/20796 | 11/1992 |
| WO | WO 95/25429 | 9/1995 |
| WO | WO 95/28483 | 10/1995 |

OTHER PUBLICATIONS

Duro et al., 1995, Oncogene, 11:21–29.*
Baldin, V. et al., "Cyclin D1 is a nuclear protein required for cell cycle progression in $G_1$," *Genes & Dev.* 7:812–821 (May 1993).
Bates, S. et al., "Absence of cyclin D/cdk complexes in cells lacking functional retinoblastoma protein," *Oncogene* 9(6):1633–1640 (Jun. 1994).
Dowdy, S.F. et al., "Physical Interaction of the Retinoblastoma Protein with Human D Cyclins," *Cell* 73(3):499–511 (May 1993).
Duro, D. et al., "A new type of p16$^{INK4}$/MTS1 gene transcript expressed in B–cell malignancies," *Oncogene* 11:21–29 (Jul. 1995).
El–Deiry, W.S. et al., "WAF1, a Potential Mediator of p53 Tumor Suppression," *Cell* 75(4):817–825 (Nov. 1993).
Ewen, M.E. et al., "Functional Interactions of the Retinoblastoma Protein with Mammalian D–type Cyclins," *Cell* 73(3):487–497 (May 1993).

Gu, Y. et al., "Inhibition of CDK2 activity in vivo by an associated 20K regulatory subunit," *Nature* 366:707–710 (Dec. 1993).
Guan, K.–L. et al., "Growth suppression by p18, a p16$^{INK4/MTS1}$– and p14$^{INK4B/MTS2}$–related CDK6 inhibitor, correlates with wild–type pRb function," *Genes & Dev.* 8(24):2939–2952 (Dec. 1994).
Hannon, G.J. and Beach, D., "p15$^{INK4B}$ is a potential effector of TGF–β–induced cell cycle arrest," *Nature* 371:257–261 (Sep. 1994).
Harper, J.W. et al., "The p21 Cdk–Interacting Protein Cip1 Is a Potent Inhibitor of G1 Cyclin–Dependent Kinases," *Cell* 75(4):805–816 (Nov. 1993).
Hirai, H. et al., "Novel INK4 Proteins, p19 and p18, Are Specific Inhibitors of the Cyclin D–Dependent Kinases CDK4 and CDK6," *Mol. Cell. Biol.* 15(5):2672–2681 (May 1995).
Kamb, A. et al., "A Cell Cycle Regulator Potentially Involved in Genesis of Many Tumor Types," *Science* 264:436–440 (Apr. 1994).
Kato, J.–Y. et al., "Direct binding of cyclin D to the retinoblastoma gene product (pRb) and pRb phosphorylation by the cyclin D–dependent kinase CDK4," *Genes & Dev.* 7(3):331–342 (Mar. 1993).
Lukas, J. et al., "DNA Tumor Virus Oncoproteins and Retinoblastoma Gene Mutations Share the Ability to Relieve the Cell's Requirement for Cyclin D1 Function in G1," *J. Cell Biol.* 125(3):625–638 (May 1994).
Mao, L. et al., "A Novel p16$^{INK4A}$ Transcript," *Cancer Res.* 55:2995–2997 (Jul. 1995).
Matsushime, H. et al., "Colony–Stimulating Factor 1 Regulates Novel Cyclins during the G1 Phase of the Cell Cycle," *Cell* 65(4):701–713 (May 1991).
Matsushime, H. et al., "Identification and Properties of an Atypical Catalytic Subunit (p34$^{PSK-J3}$/cdk4) for Mammalian D Type G1 Cyclins," *Cell* 71(2):323–334 (Oct. 1992).
Matsushime, H. et al., "D–Type Cyclin–Dependent Kinase Activity in Mammalian Cells," *Mol. Cell Biol.* 14(3):2066–2076 (Mar. 1994).

(List continued on next page.)

Primary Examiner—Anthony C. Caputa
Assistant Examiner—Natalie Davis
(74) Attorney, Agent, or Firm—Alston & Bird LLP

(57) ABSTRACT

The INK4A (MTS1, CDKN2) gene encodes a specific inhibitor (InK4a-p16) of the cyclin D-dependent kinases CDK4 and CDK6. InK4a-p16 can block these kinase from phosphorylating the retinoblastoma protein (pRb), preventing exit from the G1 phase of the cell cycle. Deletions and mutations involving the gene encoding InK4a-p16, INK4A, occur frequently in cancer cells, implying that INK4a-p16, like pRb, suppresses tumor formulation. However, a completely unrelated protein (ARF-p19) arises in major part from an alternative reading frame of the mouse INK4A gene. Expression of an ARF-p19 cDNA (SEQ ID NO:1) in rodent fibroblasts induces both G1 and G2 phase arrest.

10 Claims, 8 Drawing Sheets

OTHER PUBLICATIONS

Meyerson, M. and Harlow, E., "Identification of $G_1$ Kinase Activity for cdk6, a Novel Cyclin D Partner," *Mol. Cell. Biol.* 14(3):2077–2086 (Mar. 1994).

Nasmyth, K. and Hunt, T., "Dams and sluices," *Nature* 366:634–635 (Dec. 1993).

Noburi, T. et al., "Deletions of the cyclin–dependent kinase–4 inhibitor gene in multiple human cancers," *Nature* 368:753–756 (Apr. 1994).

Okamoto, A. et al., "Mutations and altered expression of $p16^{INK4}$ in human cancer," *Proc. Natl. Acad. Sci. USA* 91:11045–11049 (Nov. 1994).

Peters, G., "Stifled by inhibitions," *Nature* 371:204–205 (Sep. 1994).

Polyak, K. et al., "$p27^{Kip1}$, a cyclin–Cdk inhibitor, links transforming growth factor–β and contact inhibition to cell cycle arrest," *Genes & Dev.* 8(1):9–22 (Jan. 1994).

Polyak, K. et al., "Cloning of $p27^{Kip1}$, a Cyclin–Dependent Kinase Inhibitor and a Potential Mediator of Extracelluar Antimitogenic Signals," *Cell* 78(1):59–66 (Jul. 1994).

Quelle, D.E. et al., "Overexpression of mouse D–type cyclins accelerates $G_1$ phase in rodent fibroblasts," *Genes & Dev.* 7(8):1559–1571(Aug. 1993).

Quelle, D.E. et al. "Cloning and characterization of murine $p16^{INK4a}$ and $p15^{INK4b}$ genes," *Oncogene* 11:635:645 (Aug. 1995).

Quelle, D.E. et al., "Alternative Reading Frames of the INK4a Tumor Suppressor Gene Encode Two Unrelated Proteins Capable of Inducing Cell Cycle Arrest," *Cell* 83:993–1000 (Dec. 1995).

Quelle, D.E. et al., "Cancer–associated mutations at the INK4a locus cancel cell cycle arrest by $p16^{INK4a}$ but not by the alternative reading frame protein $p19^{ARF}$," *Proc. Natl. Acad. Sci. USA* 94:669–673 (Jan. 1997).

Serrano, M. et al., "A new regulatory motif in cell–cycle control causing specific inhibition of cyclin D/CDK4," *Nature* 366:704–707 (Dec. 1993).

Sherr, C.J., "Mammalian $G_1$ Cyclin," *Cell* 73:1059–1065 (Jun. 1993).

Stone, S. et al., "Complex Structure and Regulation of the P16 (MTS1) Locus," *Cancer Res.* 55:2988–2994 (Jul. 1995).

Tam, S.W. et al., "Differential expression and regulatoin of Cyclin D1 protein in normal and tumor human cells: association with cdK4 is required for Cyclin D1 function in G1 progression," *Oncogene* 9(9):2663–2674 (Sep. 1994).

Toyoshima, H. and Hunter, T., "p27, a Novel Inhibitor of G1 Cyclin–Cdk Protein Kinase Activity, Is Related to p21," *Cell* 78(1):67–74 (Jul. 1994).

Xiong, Y. et al., "Subunit rearrangement of the cyclin–dependent kinases is associated with cellular transformation," *Genes & Dev.* 7(8)1572–1583 (Aug. 1993).

Xiong, Y. et al., "p21 is a universal inhibitor of cyclin kinases,"*Nature* 366:701–704 (Dec. 1993).

* cited by examiner

SEQ. ID NO:1:

```
EXON 1b                          27                                              54
GTC ACA GTG AGG CCG CCG CTG AGG GAG TAC AGC AGC GGG AGC ATG GGT CGC AGG
                                                 SEQ ID NO:2:   M   G   R   R
5'PRIMER FOR RT-PCR              81                                              108
TTC TTG GTC ACT GTG AGG ATT CAG CGC GCG GGC CGC CCA CTC CAA GAG AGG GTT
 F   L   V   T   V   R   I   Q   R   A   G   R   P   L   Q   E   R   V
                                 135                                             162
TTC TTG GTG AAG TTC GTG CGA TCC CGG AGA CCC AGG ACA GCG AGC TGC GCT CTG
 F   L   V   K   F   V   R   S   R   R   P   R   T   A   S   C   A   L
                                 189                                             216
GCT TTC GTG AAC ATG TTG TTG AGG CTA GAG AGG ATC TTG AGA AGA GGG CCG CAC
 A   F   V   N   M   L   L   R   L   E   R   I   L   R   R   G   P   H
                ▼ EXON 2          243                                            270
CGG AAT CCT GGA CCA GGT GAT GAT GAT GGG CAA CGT TCA CGT AGC AGC TCT TCT
 R   N   P   G   P   G   D   D   D   G   Q   R   S   R   S   S   S   S
           SEQ ID NO:5:  M   M   M   G   N   V   H   V   A   A   L   L
                                 297                                             324
GCT CAA CTA CGG TGC AGA TTC GAA CTG CGA GGA CCC CAC TAC CTT CTC CCG CCC
 A   Q   L   R   C   R   F   E   L   R   G   P   H   Y   L   L   P   P
 L   N   Y   G   A   D   S   N   C   E   D   P   T   T   F   S   R   P
                                 351                                             378
GGT GCA CGA CGC AGC GCG GGA AGG CTT CCT GGA CAC GCT GGT GGT GCT GCA CGG
 G   A   R   R   S   A   G   R   L   P   G   H   A   G   G   A   A   R
 V   H   D   A   A   R   E   G   F   L   D   T   L   V   V   L   H   G
```

FIG.1A

```
                                405                                           432
GTC AGG GGC TCG GCT GGA TGT GCG CGA TGC CTG GGG TCG CCT GCC GCT CGA CTT
 V   R   G   S   A   G   C   A   R   C   L   G   S   P   A   A   R   L
  S   G   A   R   L   D   V   R   D   A   W   G   R   L   P   L   D   L
                                459                                           486
GGC CCA AGA GCG GGG ACA TCA AGA CAT CGT GCG ATA TTT GCG TTC CGC TGG GTG
 G   P   R   A   G   T   S   R   H   R   A   I   F   A   F   R   W   V
  A   Q   E   R   G   H   Q   D   I   V   R   Y   L   R   S   A   G   C
                                513                                           540
CTC TTT GTG TTC CGC TGG GTG GTC TTT GTG TAC CGC TGG GAA CGT CGC CCA GAC
 L   F   V   F   R   W   V   V   F   V   Y   R   W   E   R   R   P   D
  S   L   C   S   A   G   W   S   L   C   T   A   G   N   V   A   Q   T
                                567                                           594
CGA CGG GCA TAG CTT CAG CTC AAG CAC GCC CAG GGC CCT GGA ACT TCG CGG CCA
 R   R   A   ***
  D   G   H   S   F   S   S   S   T   P   R   A   L   E   L   R   G   Q
     3'PRIMER FOR RT-PCR       621                                            648
ATC CCA AGA GCA GAG CTA AAT CCG GCC TCA GGC CGC CTT TTT CTT CTT AGC TTC
  S   Q   E   Q   S   ***
                                675                                           702
ACT TCT AGC GAT GCT AGC GTG TCT AGC ATG TGG CTT TAA AAA ATA CAT AAT AAT
GCT TTT TTT TT
```

FIG.1B

β transcripts    E1β probe

β transcripts    Exon2 probe

α transcripts    E1α probe

α transcripts    Exon2 probe

Antiserum: | NRS | p19 | p16 | NRS | p19 | p16 | NRS | p19 | p16 |
| 1 | 2 | 3 | 4 | 5 | 6 | 7 | 8 | 9 |

— 29.5

— 18.3

— 15.4

Input: ⊢— HA-p19 —⊢— p16 —⊢— p19 —⊣

FIG.3

FIG.4A
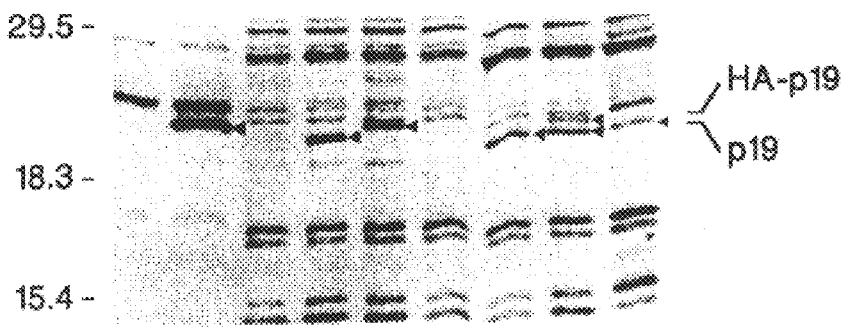
FIG.4B
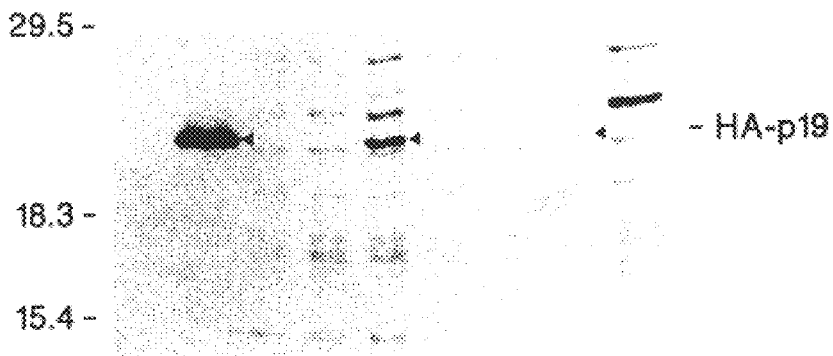
FIG.4C
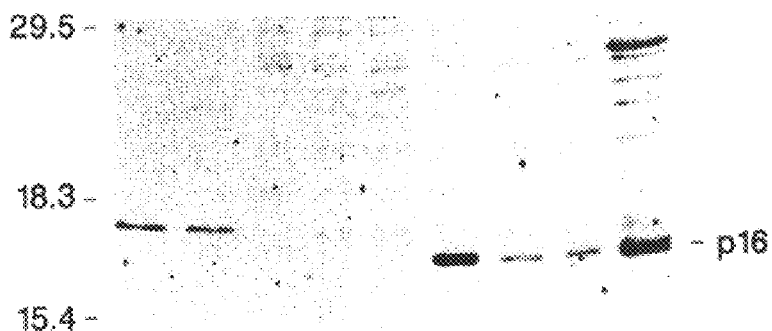

Anti-p19    Anti-p19 + Peptide    Anti-HA

```
              70              80              90
Mouse  DDDGQR  SRSSSSAQLR   CRFELRGPHY
Human  HDDGQR  PSGGAAAAPR   RGAQLRRPRH
        ■■      T*■V2         ■   HV  R Q
        L3      L
```

```
              100             110            121
       LLPPGARRSA  GRLPGHAGGA  ARVRGSAGCAR
       SHPTRARRCP  GGLPGHAGGA  APGRGAAGRAR
        ■ S*  V2    E   ■R  D     AL3  ■■2T3*
          L7  Q3        ■       S*          L
          ■   P                 A
              L
```

FIG.6

SEQ ID NO:3:

```
                                 27                                              54
         CGC GCC TGC GGG GCG GAG ATG GGC AGG GGG CGG TGC GTG GGT CCC AGT CTG CAG 81                                       108
         TTA AGG GGG CAG GAG TGG CGC TGC TCA CCT CTG GTG CCA AAG GGC GGC GCA GCG 135                             162
         GCT GCC GAG CTC GGC CCT GGA GGC GGC GAG AAC ATG GTG CGC AGG TTC TTG GTG
arf                                              SEQ ID NO:4:  M   V   R   R   F   L   V 189                             216
         ACC CTC CGG ATT CGG CGC GCG TGC GGC CCG CCG CGA GTG AGG GTT TTC GTG GTT
arf       T   L   R   I   R   R   A   C   G   P   P   R   V   R   V   F   V   V 243                             270
         CAC ATC CCG CGG CTC ACG GGG GAG TGG GCA GCG CCA GGG GCG CCC GCC GCT GTG
arf       H   I   P   R   L   T   G   E   W   A   A   P   G   A   P   A   A   V 297                             324
         GCC CTC GTG CTG ATG CTA CTG AGG AGC CAG CGT CTA GGG CAG CAG CCG CTT CCT
arf       A   L   V   L   M   L   L   R   S   Q   R   L   G   Q   Q   P   L   P 351                             378
         AGA AGA CCA GGT CAT GAT GAT GGG CAG CGC CCG AGT GGC GGA GCT GCT GCT GCT
arf       R   R   P   G   H   D   D   G   Q   R   P   S   G   G   A   A   A   A
p16                    M   M   M   G   S   A   R   V   A   E   L   L   L   L 405                             432
         CCA CGG CGC GGA GCC CAA CTG CGC CGA CCC CGC CAC TCT CAC CCG ACC CGT GCA
arf       P   R   R   G   A   Q   L   R   R   P   R   H   S   H   P   T   R   A
p16       H   G   A   E   P   N   C   A   D   P   A   T   L   T   R   P   V   H 459                             486
         CGA CGC TGC CCG GGA GGG CTT CCT GGA CAC GCT GGT GGT GCT GCA CCG GGC CGG
arf       R   R   C   P   G   G   L   P   G   H   A   G   G   A   P   G   R
p16       D   A   A   R   E   G   F   L   D   T   L   V   V   L   H   R   A   G 513                             540
         GGC GCG GCT GGA CGT GCG CGA TGC CTG GGG CCG TCT GCC CGT GGA CCT GGC TGA
arf       G   A   A   G   R   A   R   C   L   G   P   S   A   R   G   P   G   *
p16       A   R   L   D   V   R   D   A   W   G   R   L   P   V   D   L   A
```

FIG.7

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 713 base pairs
      (B) TYPE: nucleic acid
      (C) STRANDEDNESS: double
      (D) TOPOLOGY: unknown (ii) MOLECULE TYPE: DNA (genomic)

(ix) FEATURE:
      (A) NAME/KEY: CDS
      (B) LOCATION: 43..548

(ix) FEATURE:
      (A) NAME/KEY: CDS
      (B) LOCATION: 43..551

(xi) SEQUENCE DESCRIPTION: SEQ ID NO: 1:

```
GTCACAGTGA GGCCGCCGCT GAGGGAGTAC AGCAGCGGGA GC ATG GGT CGC AGG        54
                                              Met Gly Arg Arg
                                                1

TTC TTG GTG ACT GTG AGG ATT CAG CGC GCG GGC CGC CCA CTC CAA GAG      102
Phe Leu Val Thr Val Arg Ile Gln Arg Ala Gly Arg Pro Leu Gln Glu
 5              10                  15                  20

AGG GTT TTC TTG GTG AAG TTC GTG CGA TCC CGG AGA CCC AGG ACA GCG      150
Arg Val Phe Leu Val Lys Phe Val Arg Ser Arg Arg Pro Arg Thr Ala
                25                  30                  35

AGC TGC GCT CTG GCT TTC GTG AAC ATG TTG TTG AGG CTA GAG AGG ATC      198
Ser Cys Ala Leu Ala Phe Val Asn Met Leu Leu Arg Leu Glu Arg Ile
            40                  45                  50

TTG AGA AGA GGG CCG CAC CGG AAT CCT GGA CCA GGT GAT GAT GAT GGG      246
Leu Arg Arg Gly Pro His Arg Asn Pro Gly Pro Gly Asp Asp Asp Gly
        55                  60                  65

CAA CGT TCA CGT AGC AGC TCT TCT GCT CAA CTA CGG TGC AGA TTC GAA      294
Gln Arg Ser Arg Ser Ser Ser Ser Ala Gln Leu Arg Cys Arg Phe Glu
    70                  75                  80

CTG CGA GGA CCC CAC TAC CTT CTC CCG CCC GGT GCA CGA CGC AGC GCG      342
Leu Arg Gly Pro His Tyr Leu Leu Pro Pro Gly Ala Arg Arg Ser Ala
 85                  90                  95                 100

GGA AGG CTT CCT GGA CAC GCT GGT GGT GCT GCA CGG GTC AGG GGC TCG      390
Gly Arg Leu Pro Gly His Ala Gly Gly Ala Ala Arg Val Arg Gly Ser
                105                 110                 115
```

```
GCT GGA TGT GCG CGA TGC CTG GGG TCG CCT GCC GCT CGA CTT GGC CCA          438
Ala Gly Cys Ala Arg Cys Leu Gly Ser Pro Ala Ala Arg Leu Gly Pro
            120                 125                 130

AGA GCG GGG ACA TCA AGA CAT CGT GCG ATA TTT GCG TTC CGC TGG GTG          486
Arg Ala Gly Thr Ser Arg His Arg Ala Ile Phe Ala Phe Arg Trp Val
            135                 140                 145

CTC TTT GTG TTC CGC TGG GTG GTC TTT GTG TAC CGC TGG GAA CGT CGC          534
Leu Phe Val Phe Arg Trp Val Val Phe Val Tyr Arg Trp Glu Arg Arg
            150                 155                 160

CCA GAC CGA CGG GCA TAG CTTCAGCTC AAGCACGCCC AGGGCCCTGG                  581
Pro Asp Arg Arg Ala
165

AACTTCGCGG CCAATCCCAA GAGCAGAGCT AAATCCGGCC TCAGCCCGCC TTTTTCTTCT        641

TAGCTTCACT TCTAGCGATG CTAGCGTGTC TAGCATGTGG CTTTAAAAAA TACATAATAA        701

TGCTTTTTTT TT                                                            713

(2) INFORMATION FOR SEQ ID NO: 2:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO: 2:

Met Gly Arg Arg Phe Leu Val Thr Val Arg Ile Gln Arg Ala Gly Arg
1               5                   10                  15

Pro Leu Gln Glu Arg Val Phe Leu Val Lys Phe Val Arg Ser Arg Arg
                20                  25                  30

Pro Arg Thr Ala Ser Cys Ala Leu Ala Phe Val Asn Met Leu Leu Arg
            35                  40                  45

Leu Glu Arg Ile Leu Arg Arg Gly Pro His Arg Asn Pro Gly Pro Gly
        50                  55                  60

Asp Asp Asp Gly Gln Arg Ser Arg Ser Ser Ser Ala Gln Leu Arg
65                  70                  75                  80

Cys Arg Phe Glu Leu Arg Gly Pro His Tyr Leu Leu Pro Pro Gly Asp
                85                  90                  95

Arg Arg Ser Ala Gly Arg Leu Pro Gly His Ala Gly Ala Ala Arg
            100                 105                 110

Val Arg Gly Ser Ala Gly Cys Ala Arg Cys Leu Gly Ser Pro Ala Ala
            115                 120                 125

Arg Leu Gly Pro Arg Ala Gly Thr Ser Arg His Arg Ala Ile Phe Ala
        130                 135                 140

Phe Arg Trp Val Leu Phe Val Phe Arg Trp Val Val Phe Val Tyr Arg
145                 150                 155                 160

Trp Glu Arg Arg Pro Asp Arg Arg Ala
                165

(2) INFORMATION FOR SEQ ID NO: 3:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: DNA (genomic)
```

(ix) FEATURE:
    (A) NAME/KEY: CDS
    (B) LOCATION: 142..540

(xi) SEQUENCE DESCRIPTION: SEQ ID NO: 3:

```
CGCGCCTGCG GGGCGGAGAT GGGCAGGGGG CGGTGCGTGG GTCCCAGTCT GCAGTTAAGG        60

GGGCAGGAGT GGCGCTGCTC ACCTCTGGTG CCAAAGGGCG GCGCAGCGGC TGCCGAGCTC       120

GGCCCTGGAG GCGGCGAGAA C ATG GTG CGC AGG TTC TTG GTG ACC CTC CGG         171
                        Met Val Arg Arg Phe Leu Val Thr Leu Arg
                         1               5                  10

ATT CGG CGC GCG TGC GGC CCG CCG CGA GTG AGG GTT TTC GTG GTT CAC         219
Ile Arg Arg Ala Cys Gly Pro Pro Arg Val Arg Val Phe Val Val His
             15                  20                  25

ATC CCG CGG CTC ACG GGG GAG TGG GCA GCG CCA GGG GCG CCC GCC GCT         267
Ile Pro Arg Leu Thr Gly Glu Trp Ala Ala Pro Gly Ala Pro Ala Ala
         30                  35                  40

GTG GCC CTC GTG CTG ATG CTA CTG AGG AGC CAG CGT CTA GGG CAG CAG         315
Val Ala Leu Val Leu Met Leu Leu Arg Ser Gln Arg Leu Gly Gln Gln
         45                  50                  55

CCG CTT CCT AGA AGA CCA GGT CAT GAT GAT GGG CAG CGC CCG AGT GGC         363
Pro Leu Pro Arg Arg Pro Gly His Asp Asp Gly Gln Arg Pro Ser Gly
     60                  65                  70

GGA GCT GCT GCT GCT CCA CGG CGC GGA GCC CAA CTG CGC CGA CCC CGC         411
Gly Ala Ala Ala Ala Pro Arg Arg Gly Ala Gln Leu Arg Arg Pro Arg
 75                  80                  85                  90

CAC TCT CAC CCG ACC CGT GCA CGA CGC TGC CCG GGA GGG CTT CCT GGA         459
His Ser His Pro Thr Arg Ala Arg Arg Cys Pro Gly Gly Leu Pro Gly
                 95                 100                 105

CAC GCT GGT GGT GCT GCA CCG GGC CGG GGC GCG GCT GGA CGT GCG CGA         507
His Ala Gly Gly Ala Ala Pro Gly Arg Gly Ala Ala Gly Arg Ala Arg
             110                 115                 120

TGC CTG GGG CCG TCT GCC CGT GGA CCT GGC TGA                             540
Cys Leu Gly Pro Ser Ala Arg Gly Pro Gly
             125                 130
```

(2) INFORMATION FOR SEQ ID NO: 4:

(i) SEQUENCE CHARACTERISTICS:
        (A) LENGTH: 132 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Val Arg Arg Phe Leu Val Thr Leu Arg Ile Arg Arg Ala Cys Gly
 1               5                  10                  15

Pro Pro Arg Val Arg Val Phe Val Val His Ile Pro Arg Leu Thr Gly
             20                  25                  30

Glu Trp Ala Ala Pro Gly Ala Pro Ala Ala Val Ala Leu Val Leu Met
         35                  40                  45

Leu Leu Arg Ser Gln Arg Leu Gly Gln Gln Pro Leu Pro Arg Arg Pro
     50                  55                  60

Gly His Asp Asp Gly Gln Arg Pro Ser Gly Gly Ala Ala Ala Ala Pro
 65                  70                  75                  80

Arg Arg Gly Ala Gln Leu Arg Arg Pro Arg His Ser His Pro Thr Arg
                 85                  90                  95

Ala Arg Arg Cys Pro Gly Gly Leu Pro Gly His Ala Gly Gly Ala Ala
             100                 105                 110
```

```
Pro Gly Arg Gly Ala Ala Gly Arg Ala Arg Cys Leu Gly Pro Ser Ala
        115                 120                 125

Arg Gly Pro Gly
    130
```

(2) INFORMATION FOR SEQ ID NO: 5:

(i) SEQUENCE CHARACTERISTICS:
        (A) LENGTH: 125 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Met Met Gly Asn Val His Val Ala Ala Leu Leu Leu Asn Tyr Gly
 1               5                  10                  15

Ala Asp Ser Asn Cys Glu Asp Pro Thr Thr Phe Ser Arg Pro Val His
            20                  25                  30

Asp Ala Ala Arg Glu Gly Phe Leu Asp Thr Leu Val Val Leu His Gly
        35                  40                  45

Ser Gly Ala Arg Leu Asp Val Arg Asp Ala Trp Gly Arg Leu Pro Leu
    50                  55                  60

Asp Leu Ala Gln Glu Arg Gly His Gln Asp Ile Val Arg Tyr Leu Arg
65                  70                  75                  80

Ser Ala Gly Cys Ser Leu Cys Ser Ala Gly Trp Ser Leu Cys Thr Ala
                85                  90                  95

Gly Asn Val Ala Gln Thr Asp Gly His Ser Phe Ser Ser Ser Thr Pro
            100                 105                 110

Arg Ala Leu Glu Leu Arg Gly Gln Ser Gln Glu Gln Ser
        115                 120                 125
```

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 6:

GCAAAGCTTG AGGCCGGATT TAGCTCTGCT C                                      31

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 7:

AGGGATCCTT GGTCACTGTG AGGATTC                                          27

(2) INFORMATION FOR SEQ ID NO: 8:

(i) SEQUENCE CHARACTERISTICS:
        (A) LENGTH: 28 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 8:

CGGGATCCGC TGCAGACAGA CTGGCCAG                                                28

(2) INFORMATION FOR SEQ ID NO: 9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 9:

CGTCTAGAGC GTGTCCAGGA AGCCTTCC                                                28

(2) INFORMATION FOR SEQ ID NO: 10:

(i) SEQUENCE CHARACTERISTICS:
        (A) LENGTH: 14 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 10:

Val Phe Val Tyr Arg Trp Glu Arg Arg Pro Asp Arg Arg Ala
1               5                   10

(2) INFORMATION FOR SEQ ID NO: 11:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 11:

CGGGATCCGA ATTCAGCCAT GGGTTACCCA TACGACGTCC CAGACTACGC TACCGGTCGC    60

AGGTTCTTGG TCAC                                                              74

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO: 12:

GCCCGCGCGC TGAATCCTCA                                                        20

ANTIBODIES TO ARF-P19

This application is a Divisional of Application Ser. No: 09/247,154 filed Feb. 9, 1999, which is a Continuation of application Ser. No.: 08/954,470, filed Oct. 20, 1997, now issued U.S. Pat. No. 5,876,965 having an issue Date of Mar. 2, 1999, which is a Divisional Application of application Ser. No. 08/534,975 Filed on Sep. 27, 1995, now issued U.S. Pat. No. 5,723,313 having an issue Date of Mar. 3, 1998, the disclosures of which are hereby incorporated herein by reference in their entireties. Applicants claim the benefits of these Applications under 35 U.S.C. §120. +gi

STATEMENT AS TO RIGHTS TO INVENTIONS MADE UNDER FEDERALLY-SPONSORED RESEARCH AND DEVELOPMENT

This invention was made with U.S. Government support under Cancer Center CORE grant 5P30CA21765-18, awarded by the National Cancer Institute. The U.S. Government has certain rights in this invention. Support for this invention was also provided by the Howard Hughes Medical Institute and the American Lebanese Syrian Associated Charities of St. Jude Children's Research Hospital.

FIELD OF THE INVENTION

This invention relates to cancer detection and treatment and, more particularly, to a novel protein called "p19$^{ARF}$ protein," "p19$^{ARF}$" or simply "ARF-p19" that is involved in regulation of the eukaryotic cell cycle. Protein ARF-p19 is encoded by a nucleic acid derived from the gene, INK4A, which also encodes an inhibitor of D-type cyclin-dependent kinases called "p16$^{Ink4a}$ protein," "p16$^{InK4a}$" or simply "InK4a-p16."

Transcripts encoding InK4a-p16 originate from a first promoter, E1α; the present invention is based on the observation that some INK4A transcripts initiate from a second promoter, E1β, and contain an Alternative Reading Frame, ARF, which overlaps the InK4a-p16 reading frame to some degree. ARF transcripts direct the production of a protein that has ARF-p19 amino acid sequences instead of the previously-known InK4a-p16 sequences. Like InK4a-p16, ARF-p19 regulates the eukaryotic cell cycle. When overexpressed, ARF-p19 inhibits cells from proceeding past both the G1 and G2 phases of the cell cycle. However, the mechanism(s) by which ARF-p19 acts are unlike those of InK4a-p16, which acts by directly and specifically interacting with CDK (cyclin D-dependent kinase) proteins and thus preventing CDK-cyclin D interactions.

In addition to (1) ARF-p19 proteins, this invention further relates to (2) nucleic acids that encode ARF-p19 isolated from mice, humans and other mammals; (3) antibodies that specifically bind ARF-p19 protein or polypeptides derived therefrom; (4) methods for detecting one or more nucleic acids encoding ARF-p19, or alterations in such nucleic acids; (5) methods for producing ARF-p19 proteins using nucleic acids that encode ARF-p19; (6) purified ARF-p19 proteins, or fusion proteins derived from the joining of an ARF-p19 polypeptide sequence with a second polypeptide sequence; (7) methods of treating cancer using purified ARF-p19 proteins or fusion proteins derived therefrom; (8) methods of inducing cell cycle arrest using ARF-pi9 proteins or nucleic acids encoding ARF-p19 proteins; (9) methods for detecting ARF-p19 proteins using antibodies that specifically bind ARF-p19 proteins; (10) methods of selectively killing cells having uncontrolled growth using antibodies that specifically bind ARF-p19 proteins, or conjugates derived from such antibodies; (11) methods of stimulating cell growth using antibodies that specifically bind ARF-p19 proteins, or fragments derived from such antibodies; and (12) transgenic non-human animals that have a genetically engineered alteration in one or more nucleic acids encoding ARF-p19 proteins but which express normal levels of wild-type InK4a-p16 protein, or which overexpress human ARF-p19 or mutant forms of ARF-p19.

BACKGROUND OF THE INVENTION

Neoplasia, the pathological process by which tumors develop, necessarily involves unregulated, or at best misregulated, cellular growth and division. The molecular pathways that regulate cellular growth must inevitably intersect with those that regulate the cell cycle. The cell cycle consists of a cell division phase and the events that occur during the period between successive cell divisions, known as interphase. Interphase is composed of successive G1, S, and G2 phases, and normally comprises 90% or more of the total cell cycle time. Most cell components are made continuously throughout interphase; it is therefore difficult to define distinct stages in the progression of the growing cell through interphase. One exception is DNA synthesis, since the DNA in the cell nucleus is replicated only during a limited portion of interphase. This period is denoted as the S phase (S=synthesis) of the cell cycle. The other distinct stage of the cell cycle is the cell division phase, which includes both nuclear division (mitosis) and the cytoplasmic division (cytokinesis) that follows. The entire cell division phase is denoted as the M phase (M=mitotic). This leaves the period between the M phase and the start of DNA synthesis, which is called the G1 phase (G=gap), and the period between the completion of DNA synthesis and the next M phase, which is called the G2 phase (Alberts, B. et al., *Molecular Biology of the Cell*, Garland Publishing, Inc., New York & London (1983), pages 611–612.).

Progression through different transitions in the eukaryotic cell cycle is positively regulated by a family of master enzymes, the cyclin-dependent kinases (reviewed by Sherr, C. J., *Cell* 73:1059–1065 (1993)). These holoenzymes are composed of two proteins, a regulatory subunit (the cyclin), and an associated catalytic subunit (the actual cyclin-dependent kinase or CDK), the levels of which vary with different phases of the cell cycle (Peters, G., *Nature* 371:204–205 (1994)). Both cyclins and CDKs represent molecular families that encompass a variety of genetically related but functionally distinct proteins. Generally, different types of cyclins are designated by letters (i.e., cyclin A, cyclin B, cyclin D, cyclin E, etc.); CDKs are distinguished by numbers (CDK1, CDK2, CDK3, CDK4, CDK5, etc.; CDK1 is a.k.a. CDC2).

CDK-cyclin D complexes regulate the decision of cells to replicate their chromosomal DNA (Sherr, *Cell* 73:1059–1065 (1993)). As cells enter the cycle from quiescence, the accumulation of CDK-cyclin D holoenzymes occurs in response to mitogenic stimulation, with their kinase activities being first detected in mid-G1 phase and increasing as cells approach the G1/S boundary (Matsushime et al., Mol. Cell. Biol. 14:2066–2076 (1994); Meyerson and Harlow, *Mol. Cell. Biol.* 14:2077–2086 (1994)). The cyclin D regulatory subunits are highly labile, and premature withdrawal of growth factors in G1 phase results in a rapid decay of CDK-cyclin D activity that correlates with the failure to enter S phase. In contrast, removal of growth factors late in G1 phase, although resulting in a similar collapse of CDK-cyclin D activity, has no effect on further progression through the cell cycle (Matsushime et al., *Cell* 65:701–713 (1991)). Microinjection of antibodies to cyclin D1 into fibroblasts during G1 prevents entry into the S phase, but injections performed at or after the G1→S transition are without effect (Baldin et al., *Genes & Devel.* 7:812–821 (1993); Quelle et al., *Genes & Devel.* 7:1559–1571 (1993)). Therefore, CDK-cyclin D complexes execute their critical functions at a late G1 checkpoint, after which cells become independent of mitogens for completion of the cycle.

In mammals, cells enter the cell cycle and progress through G1 phase in response to extracellular growth signals which trigger the transcriptional induction of D-type cyclins. The accumulation of D cyclins leads to their association with two distinct catalytic partners, CDK4 and CDK6, to form kinase holoenzymes. Several observations argue for a significant role of the cyclin D-dependent kinases in phosphorylating the retinoblastoma protein, pRb, leading to the release of pRB-associated transcription factors that are necessary to facilitate progression through the G1→S transition. First, CDK-cyclin D complexes have a distinct substrate preference for pRb but do not phosphorylate the canonical CDK substrate, histone H1 (Matsushime et al., *Cell* 71:323–334 (1992); Matsushime et al., *Mol. Cell. Biol.* 14:2066–2076 (1994); Meyerson and Harlow, *Mol. Cell. Biol.* 14:2077–2086 (1994)). Their substrate specificity may be mediated in part by the ability of D-type cyclins to bind to pRb directly, an interaction which is facilitated by a Leu-X-Cys-X-Glu pentapeptide that the D cyclins share with DNA oncoproteins that also bind pRb (Dowdy et al., *Cell* 73:499–511 (1993); Ewen et al., *Cell* 73:487–497 (1993); Kato et al., *Genes & Devel.* 7:331–342 (1993)). Second, cells in which pRb function has been disrupted by mutation, deletion, or after transformation by DNA tumor viruses are no longer inhibited from entering S phase by microinjection of antibodies to D cyclin, indicating that they have lost their dependency on the cyclin D-regulated G1 checkpoint (Lukas et al., *J. Cell. Biol.* 125:625–638 (1994); Tam et al., *Oncogene* 9:2663–2674 (1994)). However, introduction of pRb into such cells restores their requirement for cyclin D function (Lukas et al., *J. Cell. Biol.* 125:625–638 (1994)). Third, pRb-negative cells synthesize elevated levels of a 16 kDa polypeptide inhibitor of CDK4, "p16$^{InK4a}$" (a.k.a. "InK4a-p16" or simply "p16"), which is a member of a recently discovered class of cell cycle regulatory proteins (Nasmyth and Hunt, *Nature* 366:634–635 (1993); Peters, G., *Nature* 371:204–205 (1994)) and which is found in complexes with CDK4 at the expense of D-type cyclins during G1 phase (Bates et al., *Oncogene* 9:1633–1640 (1994); Serrano et al., *Nature* 366:704–707 (1993); Xiong et al., *Genes & Devel.* 7:1572–1583 (1993)). The fact that such cells cycle in the face of apparent CDK4 inhibition again implies that D-type cyclins are dispensable in the Rb-negative setting.

The InK4 gene family ("InK4" signifies Inhibitors of CDK4) is known to include at least three other low molecular weight polypeptides, InK4b-p15, induced in human epithelial cells treated by transforming growth factory-β (TGF-β) (Hannon, G. J., and Beach, D., *Nature* 371:257–261 (1994)), InK4d-p19 (Hirai, H., et al., *Mol. Cell. Biol.* 15:2672–2681 (1995)) and InK4c-p18 (Guan et al., *Genes & Develop.* 8:2939–2952 (1994); Hirai, H., et al., *Mol. Cell. Biol.* 15:2672–2681 (1995)). InK4d-p19 and InK4c-p18 are described in detail in Ser. No. 08/384,106, filed Feb. 6, 1995, which is hereby incorporated by reference.

Members of the InK4 family are typically composed of repeated ankyrin motifs, each of about 32 amino acids in length. All known members of the InK4 family act to specifically inhibit enzymatic activities of D-type cyclin-dependent kinases such as CDK4 and CDK6. Unlike other universal CDK inhibitors, such as p21$^{Cip1/Waf1}$ (E1-Deiry et al., *Cell* 75:817–825 (1993); Gu et al., *Nature* 366:707–710 (1993); Harper et al., *Cell* 75:805–816 (1993); Xiong et al., *Nature* 366:701–704 (1993)) and p27$^{Kip1}$ (Polyak et al., *Genes & Devel.* 8:9–22 (1994); Polyak et al., *Cell* 78:59–66 (1994); Toyoshima and Hunter, *Cell* 78:67–74 (1994)), the InK4 proteins selectively inhibit the activities of CDK4 and CDK6, but do not inhibit the activities of other CDKs (Guan et al., *Genes & Devel.* 8:2939–2952 (1994); Hannon and Beach, *Nature* 371:257–261 (1994); Serrano et al., *Nature* 366:704–707 (1993)).

Like many CDK inhibitors (CKIs) (Nasmyth and Hunt, *Nature* 366:634–635 (1993)), InK4 family members negatively regulate progression through the mammalian cell cycle, in part in response to anti-proliferative extracellular signals. The InK4 proteins, by inhibiting the activities of a specific class of the D-type cyclin-dependent kinases (i.e., CDK4 and/or CDK6), arrest cell cycle progression in G1 phase and thus prevent cells from replicating their chromosomal DNA. Thus, in contradistinction to the positive regulation of D-type cyclin synthesis by growth factors, extracellular inhibitors of G1 progression can negatively regulate the activity of D-type cyclin-dependent kinases by inducing InK4 proteins.

RELATED ART

Mullis et al., U.S. Pat. No. 4,965,188 (Oct. 23, 1990), describe methods for amplifying nucleic acid sequences using the polymerase chain reaction (PCR).

Beach, published PCT patent application WO 92/20796 (Nov. 26, 1992), describes genes encoding D cyclins and uses thereof.

Berns, U.S. Pat. No. 5,174,986 (Dec. 29, 1992), describes methods for determining the oncogenic potential of chemical compounds using a transgenic mouse predisposed to develop T-cell lymphomas.

Crissman et al., U.S. Pat. No. 5,185,260 (Feb. 9, 1993), describe methods for distinguishing and selectively killing transformed (neoplastic) cells using synthetic G1 kinase inhibitors.

Stone, S., et al., *Cancer Research* 55:2988–2994 (1995), describe two cDNAs derived from the human INK4A gene, including an "αform" encoding InK4a-p16 and β", form" that includes an open reading frame (designated "ORF 2") that overlaps the reading frame encoding the ARF-p19 protein described herein. Stone et al. state that it "is unknown if ORF 2 encodes a protein" (legend to FIG. 1, page 2990) and indicate that "ORF 2 has not been selectively maintained and probably does not encode a protein" (page 2989, column 2, lines 20–21).

Mao, L., et al., *Cancer Research* 55:2995–2997 (1995), describe two transcripts and corresponding cDNAs derived from the human INK4A gene, designated "p16" and "p16β." The p16 transcript is stated to encode the InK4a-p16 protein, while the p16β transcript is stated to contain a "theoretical open reading frame" (page 1996, column 1, line 47) that is not further defined, and suggest this sequence "probably represents an untranslated open reading frame" (page 2997, column 2, lines 9–10). Mao et al. state that the in vitro transcription and translation (TNT) product of the p16β cDNA is recognized by an antibody to InK4a-p16 polypeptide sequences (page 2997, column 1, lines 6), suggesting that the p16β transcript encodes an amino-terminal truncated InK4a-p16 polypeptide rather than a protein having, as ARF-p19 does, an amino acid sequence unrelated to that of InK4a-p16. However, Mao et al. also state that, using InK4a-p16 antiserum, they are unable to identify an amino-terminal truncated p16β protein in cell lines (page 2997, column 2, lines 1–2). Thus, Mao et al. are silent regarding the ARF-p19 protein described herein.

SUMMARY OF THE INVENTION

The present invention relates to the discovery in mammalian cells of a novel cell cycle regulatory protein, having a predicted molecular mass of 19 kDa, here designated "ARF-p19 protein" or more simply "ARF-p19". In particular, the invention relates to ARF-p19 proteins isolated from cells derived from a mouse or a human. Although derived from the gene encoding the previously-known InK4a-p16 protein, ARF-p19 arises by differential transcription and translation of InK4a-p16 sequences. That is, ARF-p19 is encoded by an alternative reading frame (ARF) and has an amino acid sequence (SEQ ID NO:2; SEQ ID NO:4) that is wholly unrelated to that of InK4a-p16. Surprisingly, however, ARF-p19 protein functions to regulate the cell cycle in a similar but less specific manner than, and by a mechanism distinct from that of, InK4a-p16 protein.

Thus, one aspect of the invention is directed to methods of using the ARF-p19 proteins of the invention to inhibit the growth of cancer cells and/or to prevent cancer cells from replicating their chromosomal DNA. Both InK4-p16 and InK4-p15 appear to act as tumor suppressors (Noburi, T. et al., *Nature* 368:753–756 (1994); Karnb, A. et al., *Science* 264:436440 (1994)). The genes encoding p16 and p15 map in a tandem array to the short arm of human chromosome 9 within a region that is frequently deleted in cancer cells, and the resulting loss of their anti-proliferative functions can contribute to tumorigenesis (Noburi et al., *Nature* 368:753–756 (1994), Okuda, T., et al., *Blood* 85:2321–2330 (1995)). The novel ARF-p19 protein described herein (1) plays a role in preventing the G1→S and G2→M phase transitions in normal mammalian cells, and (2) if having reduced or altered activity due to one or more mutations affecting the alternative reading frame encoding ARF-p19, could contribute to oncogenesis in some cancers, even if such mutations have no effect on the reading frame encoding InK4a-p16.

In another aspect, the invention provides nucleic acid sequences encoding ARF-p19 polypeptides from mice, humans and other mammals. The nucleic acid sequences of the invention may be expressed in the form of isolated nucleic acids, such as cDNA clones, genomic DNA clones, MRNA transcribed from either cDNA or genomic DNA clones, synthetic oligonucleotides, and/or synthetic amplification products resulting from PCR, and may be single-stranded or double-stranded.

In a related aspect, the invention provides methods for detecting nucleic acids encoding wild-type or mutant ARF-p19 proteins using the nucleic acid sequences of the invention described above. The detection of point mutations, deletions of, or other mutations in, the reading frame encoding ARF-p19 is predictive of a predisposition to, or diagnostic of, certain types of cancer.

In another related aspect, the DNA molecules of the invention described above may be cloned into expression vectors and placed in an appropriate host in order to produce ARF-p19 proteins or fusion proteins containing ARF-p19 polypeptide sequences. When placed in an animal that has cancer, this aspect of the invention relates to gene therapy for certain types of cancers.

In another aspect, the invention provides antibody compositions that bind specifically to ARF-p19 proteins and/or polypeptides derived therefrom. The antibody compositions of the invention may be polyclonal, monoclonal, or mono-specific. Although all of the antibody compositions of the invention bind specifically to ARF-p19, some compositions bind to a specific epitope of ARF-p19 and thereby inhibit a specific function of ARF-p19.

In a related aspect, the invention provides methods for detecting ARF-p19 proteins using the antibody compositions described above. The detection of reduced amounts of, or altered forms of, ARF-p19 proteins is predictive of a predisposition to, or diagnostic of, certain types of cancer.

In another aspect, the invention provides transgenic non-human animals which have one or more mutations in the endogenous reading frame encoding ARF-p19, wherein said mutation results in the production of a mutant ARF-p19 protein or results in a loss of ARF-p19 expression but does not significantly affect the InK4a-p16 gene product or expression thereof. Additionally or alternatively, the transgenic non-human animals of the invention express a human wild-type or mutant ARF-p19. Because of the transgene(s) introduced into the genome of the non-human animals of the invention, the animals have a reduced and/or altered ARF-p19 activity compared to wild-type animals, and consequentially develops certain types of cancers, particularly melanomas, in a reproducible and thus predictable manner.

In a related aspect, compositions are evaluated for their potential to enhance or inhibit certain types of cancers, particularly melanomas, using the transgenic non-human animals of the invention.

BRIEF DESCRIPTION OF THE FIGURES

FIG. 1 shows the sequence of a murine cDNA molecule (SEQ ID NO:1) homologous to human INK4A β transcripts and the sequence of the polypeptide, ARF-p19 (SEQ ID NO:2), encoded thereby; the partial carboxy-terminal amino acid sequence of InK4a-p16 (SEQ ID NO:5), encoded by exons 2 and 3 in INK4A α transcripts, is also indicated. Sequences from exon 1β (nucleotides 1–232) are spliced to exon 2 to create an open reading frame capable of encoding a novel 169 amino acid protein (ARF-p19). The initiator codon for ARF-p19 occurs at nucleotides 43–45, and a putative UAG stop codon is found at nt 550–552. Nucleotides 436–438 (double underlined CCA) are replaced by a TGA termination codon in corresponding position in the human INK4A gene (Serrano et al., *Nature* 366:704–707 (1993)); accordingly, the human ARF-p19 protein is truncated relative to the murine ARF-p19 protein. Unrelated sequences from exon 1α (not shown) are spliced to the same exon 2 acceptor site to open another reading frame that encodes InK4a-p16. Exon 2-coded InK4a-p16 amino acid sequences are shown below those of ARF-p19. The carboxyl terminus of mouse InK4a-p16 is 20 residues longer than the human polypeptide (Quelle et al., *Oncogene* 11:635–645 (1995)), with the last four amino acids of the latter encoded by a third exon (Kamb, A. et al., *Science* 264:436–440 (1994a)). The location of residues corresponding to the primers used to specifically amplify β transcripts by RT-PCR (FIG. 2) are underlined.

Figure 2A:
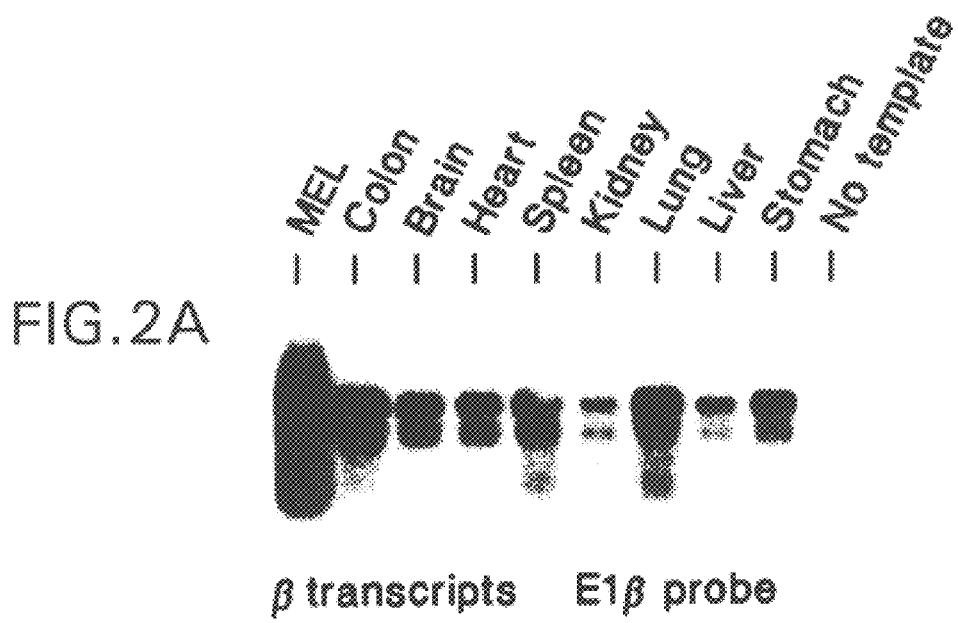
FIG. 2 (panels A–D) shows the results of RT-PCR assays of INK4A α and β mRNA transcripts in mouse tissues and the mouse MEL cell line. Equivalent quantities of RNA from the indicated tissues were amplified in parallel by RT-PCR using 5' primers specific for α or β transcripts and a common 3' primer (FIG. 1). Products from β (panels A, B) and α

(panels C, D) RT templates were hybridized with specific exon 1β (panel A), exon 1α (panel C), or exon 2 probes (panels B, D). Autoradiographic exposure times were 2 hrs.

FIG. 3 shows the results of immunoassays using antibodies to the carboxyl-terminal portion of ARF-p19 (p19 antiserum) or antibodies to InK4a-p16 (p16 antiserum) and the detection of InK4a-p16 (p16), ARF-p19 (p19) or ARF-p19 tagged with hemagglutinin (HA-p19). cDNAs encoding InK4a-p16, ARF-p19, and HA-tagged ARF-p19 (as indicated below the panel) were transcribed and translated in vitro. Proteins labeled with [$^{35}$S]-Methionine, normalized for equal input of radioactivity, were precipitated with nonimmune rabbit serum (NRS) or with antisera to InK4a-p16 or ARF-p19 (as indicated at the top) and separated on denaturing gels. The positions of marker proteins of known molecular mass are indicated at the right. is FIG. 4 (panels A–C) shows the results of immunoassays using antibodies specific for ARF-p19, InK4a-p16, or hemagglutinin (HA). Cell lysates (indicated at the bottom of panel C) were divided into three equal aliquots, separated on denaturing gels, and immunoblotted with antibodies specific for ARF-p19 (panel A), HA (panel B) or InK4a-p16 (panel C). The cell lines indicated on the bottom of the Figure (Sf9=insect cells in which baculoviral expression occurs; N3T3-d=NIH-3T3 cells genetically engineered to overexpress cyclin D1; B3T3=derivative of Balb-3T3 cells; MEL=mouse erythroleukemia cells) were either uninfected ("none") or infected with appropriate expression constructs expressing ARF-p19 ("p19"), ARF-p19 tagged with hemagglutinin ("HA-p19"), or InK4a-p16 ("p16"). Cells were infected for 48 hrs before lysis with control vectors lacking inserts (lanes 1, 3, and 7) or containing the indicated cDNAs (top, panel A). The positions of marker proteins are shown at the left and positions of ARF-p19 or InK4a-p16 at the right and by arrowheads in panels A and B. Blots were developed using enhanced fluorography (exposure time, 3 secs), allowing only approximate comparisons of signal intensities between the different panels.

FIG. 5 (panels A–C) shows the localization of ARF-p19 and p19-hemagglutinin fusion proteins to cellular nuclei. Cytospin preparations of NIH-3T3 cells infected for 48 hrs with a vector encoding HA-tagged ARF-p19 were fixed and stained with antiserum to ARF-p19 (panel A), anti-ARF-p19 plus cognate peptide (panel B), or anti-HA serum (panel C). Matched exposures are shown at 600X magnification. The addition of polypeptides having ARF-p19 sequences blocks the signal produced by the antibodies specific for ARF-p19 (panel B).

FIG. 6 summarizes mutant amino acid residues in ARF-p19 predicted from mutations in the gene that encodes both p16-InK4a and ARF-p19 compiled from data from primary tumors, xenografts, and established cell lines. The majority of INK4A mutations so far described target the 5' portion of INK4A exon 2 (Hirama and Koeffler, *Blood* 86:841–854 (1995)), which encodes portions of both InK4a-p16 and ARF-p19. Comparison of the mouse (upper) and human (lower) ARF-p19 amino acid sequences defines conserved residues (bold type). Residues in the human gene that have sustained mutations in cancer cells are doubly underlined and the mutant amino acids are indicated below them. Mutations that are silent with regard to the InK4a-p16 coding frame but which are predicted to affect the primary structure of ARF-p19 are indicated by asterisks (e.g., P71T*). Superscripts note multiple substitutions of the same residue (e.g. G68L$^3$ was independently observed in 3 cases), and closed squares define microdeletions plus frame shifts. No nonsense mutations were found. All mutations were detected in sporadic cancers except for R114L (G101W in p16), which has been genetically implicated in familial melanoma in 3 of 9 kindreds (Hussussian et al., *Nature Genet* 8:15–21 (1994); Kamb et al., *Nature Genet* 8:22–26 (1994b)). Known sequence polymorphisms have been excluded. The remaining data were taken from Caldas et al., *Nature Genet* 8:27–32 (1994), Hayashi et al., *Biochem. Biophrys. Res Commun.* 202:1426–1430 (1994), Kanb, A. et al., *Science* 264:436–440 (1994), Mori et al., *Cancer Res.* 54:3396–3397 (1994), Ohta et al., *Cancer Res* 54:5269–5272 (1994), and Zhang et al., *Cancer Res* 54:5050–5053 (1994). Numbering of InK4a-p16 amino acid sequences in the text is based on the corrected N-terminus (Hannon and Beach, Nature 371:257–261 (1994)) which includes 8 residues beyond those originally identified (Serrano et al., *Nature* 366:704–707 (1993)).

FIG. 7 shows the sequence of a human cDNA molecule (3; see also Mao et al., *Cancer Research* 55:2995–2997 91995)) corresponding to human INK4A β transcripts and the sequence of the polypeptide, ARF-p19 (SEQ ID NO:4, denoted "arf" in the Figure), which is (as described herein) encoded thereby. The partial carboxyl-terminal amino acid sequence of human InK4a-p16 ("p16") is also indicated.

DETAILED DESCRIPTION OF THE DISCLOSURE

Terms and Symbols

For purposes of this disclosure, the following abbreviations and definitions are used herein unless otherwise indicated.

The following list indicates the correspondence between the one-letter amino acid code (used in FIGS. 1, 6 and 7 and Example 6) and the three-letter amino acid code (used elsewhere herein, in accordance with 37 C.F.R. § 1.822, revised as of Jul. 1, 1994):

| A = Ala | C = Cys | D = Asp | E = Glu | F = Phe |
| G = Gly | H = His | I = Ile | K = Lys | L = Leu |
| M = Met | N = Asn | P = Pro | Q = Gln | R = Arg |
| S = Ser | T = Thr | V = Val | W = Trp | Y = Tyr |

| ABBREVIATIONS | | |
|---|---|---|
| CDK | = | cyclin-dependent kinase (protein); cdk = gene |
| cDNA | = | complementary deoxyribonucleic acid |
| DNA | = | deoxyribonucleic acid |
| DMEM | = | Dulbecco's modified Eagle's medium |
| EDTA | = | ethylenediamine tetraacetic acid |
| ES | = | embryonic stem |
| FISH | = | fluorescent in situ hybridization |
| InK | = | inhibitor of CDK (protein); INK = gene |
| kb | = | kilobase(s) |
| kDa | = | kilodalton(s) |
| MEL | = | mouse erythroleukemia (cell line) |
| nt | = | nucleotide(s) |
| PBS | = | phosphate-buffered saline |
| PCR | = | polymerase chain reaction |
| pRB | = | retinoblastoma protein |
| RT | = | reverse transcriptase |
| SDS | = | sodium dodecyl sulfate |
| Sf9 | = | *Spodoptera frugiperda* (cell line) |
| Tg | = | transgenic |
| TK | = | thymidine kinase |

Throughout the disclosure, abbreviations for nucleotide residues present in nucleic acid sequences are as described in 37 C.F.R. § 1.822, revised as of Jul. 1, 1994.

Glossary

Amino acid sequence: The sequence of a polypeptide given in the order of from amino terminal (N-terminal), to carboxyl terminal (C-terminal), Synonymous with "polypeptide sequence, " "peptide sequence," "protein sequence," or "primary protein sequence."

Animal: (1) Excludes human beings, individually and collectively, in all stages of development, including embryonic and fetal stages, unless otherwise indicated; and (2) includes all other vertebrate animals, including an individual animal in any stage of development, including embryonic and fetal stages. "Non-human animal" has the same meaning as "animal."

Animal model: A non-human animal that faithfully mimics a human disease and in which potential therapeutic compositions or potentially harmful compositions may be evaluated for their effect on the disease.

Antibody: A protein molecule synthesized by a B-cell upon exposure to antigen capable of combining specifically with that antigen. Synonymous with immunoglobulin (Ig).

Antibody, polyclonal: A composition that comprises an assortment of different antibodies that all recognize a particular antigen.

Antibody, monoclonal: A unique, isolated antibody molecule produced by a hybridoma.

Antibody, monospecific: A polyclonal antibody produced in immunological response to a single or few epitopes found in (1) a short, isolated, synthetic antigen or (2) a short, isolated, carrier-bound hapten.

Antigen: A molecule or composition of matter which (1) induces an immune response in an animal, and (2) interacts specifically with antigen-recognizing components of an immune animal's immune system.

Asyntactic: Not having the same arrangement (syntax); "out of register." In particular, note that fusion proteins cannot result from the asyntactic linkage of two (or more) open reading frames.

Carrier: A molecule required in combination with a hapten in order for an immune response to the hapten to occur. That is, a molecule which puts a hapten in a molecular context in which the hapten has enhanced immunogenicity.

Detectable label: A chemical moiety that is coupled to a biomolecule to enable detection of the biomolecule and which may be selected from the group consisting of a radiolabel, an enzyme such as horseradish peroxidase or alkaline phosphatase, streptavidin, biotin, an epitope recognized by an antibody, and equivalents thereof.

Detectably labeled: A state of a biomolecule in which the biomolecule has covalently attached to it a detectable label.

Disease: (1) Excludes pregnancy per se but not autoimmune and other diseases associated with pregnancy; (2) includes any abnormal condition of an organism or part, especially as a consequence of infection, inherent weakness, environmental stress, that impairs normal physiological functioning; and (3) includes cancers and tumors.

DNA sequence: The sequence of contiguous nucleotide bases of a strand of DNA as read from 5' to 3'. Synonymous with "DNA molecule."

Enzyme: Protein that is a catalyst for a specific chemical reaction, often one involving one or more biomolecules as substrates and/or products. Unlike non-biologically derived catalysts, enzymes may recognize a substrate with stereospecificity, i.e., some enzymes are capable of recognizing, and thus catalyzing the chemical reaction of, only one of a pair of L- and D-enantiomers.

Epitope: A part of an antigen that interacts specifically with antigen-recognizing components of an animal's immune system. In a polypeptidic antigen, epitopes may correspond to short sequences of contiguous amino acids; the remainder of the antigen is called the carrier. Synonymous with antigenic determinant.

Expression vector: An artificial DNA sequence, or a naturally-occurring DNA sequence that has been artificially modified, into which foreign or abnormal genes can be inserted and that contains transcription and translation signals that direct the expression of the inserted genes in host cells appropriate for the expression vector, and the DNA of which is replicated, either extra- or intra-chromosomally, in such appropriate host cells.

Expression construct: A construct consisting essentially of an expression vector and one or more foreign or abnormal genes inserted therein in such a manner that the expression vector's transcription and translation signals are operably linked to the inserted gene(s).

Foreign or abnormal: Not endogenous to a healthy, wild-type organism. "Foreign or abnormal genes" designates nucleic acid sequences that are not endogenous to an organism's genome, or originally endogenous nucleic acid sequences that have been rearranged, mutated, or otherwise genetically engineered so as to possess properties (i.e., genomic location, regulation of expression, copy number, etc.) not possessed by the endogenous nucleic acid sequences from which they were derived.

Gene: A DNA sequence that consists of a structural gene, e.g., a reading frame that encodes a polypeptide sequence, according to the standard genetic code; and expression elements, e.g., promoters, terminators, enhancers, etc., required for transcription of the structural gene.

Genetically engineered: Subject to human manipulation intended to introduce genetic change.

Hapten: A small molecule which (1) cannot, by itself, induce an immune response in an animal, (2) can, in combination to a carrier to which it is bound, induce an immune response in an animal, and (3) interacts specifically with the antigen-recognizing components of an immune animal's immune system.

Host animal: An animal that harbors foreign and/or abnormal genes introduced as a result of (1) invasion of cells of the animal by a naturally occurring or genetically engineered intracellular parasite; or (2) introduction into cells of foreign or abnormal genes by human manipulation.

Immune animal: An animal which has been presented with an immunizing amount of antigen and has generated a humoral and/or cell-mediated immune response thereto.

Mammal: (1) Excludes human beings, individually and collectively, in all stages of development, including embryonic and fetal stages, unless otherwise indicated; and (2) includes all other animals that are members of the vertebrae class Mammalia, including an individual animal in any stage of development, including embryonic and fetal stages, wherein members of the class are distinguished by self-regulating body temperature, hair, and, in the females, milk-producing mammae.

Microorganism: A single-celled organism (e.g., a bacterium) or an intracellular parasite (e.g., a rickettsia or a virus); includes both "live" and "attenuated" microorganisms.

Operably linked: Arranged so as to have a functional relationship; in expression constructs, inserted foreign or abnormal genes that are properly positioned with regard to the signals that control transcription and translation so that efficient expression of the inserted genes occurs are said to be operably linked to such signals (and vice-versa).

Potypeptide: A polymer of amino acid residues.

Protein: A biomolecule comprising one or more polypeptides arranged into a functional, three-dimensional form.

Restriction endonuclease: An endonuclease that cleaves DNA at each occurrence therein of a specific recognition sequence. Synonymous with "restriction enzyme."

Syntactic: Having the same arrangement (syntax); "in register." In particular, note that fusion proteins can result from the syntactic linkage of two (or more) open reading frames.

Transgene: A gene that does not occur naturally in an animal, i.e., a foreign or abnormal gene, introduced into an animal by nonnatural means, i.e., by human manipulation.

Transgenic animal: An animal into which has been introduced, by nonnatural means, i.e., by human manipulation, one or more transgenes.

DETAILED DESCRIPTION OF THE PREFERRED EMBODIMENTS

In its broadest form, the invention comprises a novel mammalian protein known as "ARF-p19," that regulates the cell cycle; nucleic acid molecules having sequences encoding polypeptide sequences of ARF-p19; antibodies specific for ARF-p19; transgenic non-human animals with alterations in the gene encoding ARF-p19; methods of making ARF-p19 nucleic acids and polypeptides; methods of making ARF-p19-specific antibodies; methods of making transgenic non-human animals with alterations in the gene encoding ARF-p19; and methods of using the nucleic acids, proteins, antibodies and transgenic animals of the invention to detect ARF-p19 nucleic acids or proteins in a sample, to diagnose cancers or predispositions thereto, to evaluate compositions for their therapeutic or oncogenic potential, and to prepare therapeutic compositions for the treatment of tumors and cancers.

Nucleic Acids and Related Embodiments

In one embodiment, the invention comprises nucleic acids having sequences encoding mouse ARF-p19, human ARF-p19 or ARF-p19 polypeptides from other mammals. For example, the invention provides cDNA molecules encoding mouse ARF-p19 (SEQ ID NO:1). The ARF-p19 cDNAs of the invention are in turn used to isolate additional nucleic acids that encode ARF-p19 polypeptide sequences, such as mouse and human genomic DNA clones. Moreover, because the homology between the nucleotide sequences of mouse and human ARF-p19 genes is quite high, the mouse and human nucleic acids may be used to design probes or degenerate primers for PCR in order to isolate cDNA and genomic clones of ARF-p19 genes from other mammals.

One skilled in the art can readily adapt the nucleic acid sequences of the invention to any system which is capable of producing nucleic acids to produce the nucleic acids of the invention. The nucleic acids of the invention, which may optionally comprise a detectable label, may be prepared as cDNA clones, genomic clones, RNA transcribed from either cDNA or genomic clones, synthetic oligonucleotides, and/or synthetic amplification products resulting, e.g., from PCR. The nucleic acids of the invention may be prepared in either single- or double-stranded form.

Methods of preparing cDNA clones are known in the art (see, for example, Chapter 8 in Sambrook et al., *Molecular Cloning: A Laboratory Manual*, Vol. 2, 2d. Ed., Cold Spring Harbor Laboratory Press, Cold Spring Harbor, N.Y. (1989), pages 8.1–8.86). Methods of analyzing genomic DNA sequences and preparing genomic clones are known in the art (see, for example, Chapter 9 in Sambrook et al., *Molecular Cloning: A Laboratory Manual*, Vol. 2, 2d. Ed., Cold Spring Harbor Laboratory Press, Cold Spring Harbor, N.Y. (1989), pages 9.1–9.62; and Chapter 2 in *Current Protocols in Molecular Biology*, Vol. 1, Ausubel et al., eds., John Wiley & Sons, Inc., Boston, Mass. (1994), pages 2.1.1–2.14.8). Genomnic DNA sequences, i.e., chromosomally-derived nucleic acids, are isolated (see Example 9) from mice and other non-human animals and used for the production of transgenic non-human animals. RNA containing ARF-p19 sequences may be prepared from cells expressing ARF-p19 according to methods known in the art (see, e.g., Chapter 4 in *Current Protocols in Molecular Biology*, Vol. 1, Ausubel et al., eds., John Wiley & Sons, Inc., Boston, Mass. (1994), pages 4.1.1–4.10.11), or may be generated by in vitro transcription using the DNA molecules of the invention (see, e.g., Chapter 10 in Sambrook et al., *Molecular Cloning: A Laboratory Manual*, Vol. 2, 2d. Ed., Cold Spring Harbor Laboratory Press, Cold Spring Harbor, N.Y. (1989), pages 10.1–10.70).

Synthetic oligonucleotides having ARF-p19-specific nucleotide sequences can be prepared using the nucleic acid sequences of the invention by known methods (see, e.g., Chapter 11 in Sambrook et al., *Molecular Cloning: A Laboratory Manual*, Vol. 2, 2d. Ed., Cold Spring Harbor Laboratory Press, Cold Spring Harbor, N.Y. (1989), pages 11.1–11.61). When used as primers in the polymerase chain reaction (PCR), the synthetic oligonucleotides preferably contain from about 15 to about 30 contiguous nucleotides exactly corresponding to unique portions of the ARF-p19 sequences of the invention, but may optionally contain additional nucleotides 5' therefrom (Innis, M. A. and Gelfand, D. H., Chapter 1 in *PCR Protocols: A Guide to Methods and Applications*, Innis et al., eds., Academic Press, Inc., New York (1990), pages 3–12; Saiki, R. K., Chapter 2 in *PCR Protocols: A Guide to Methods and Applications*, Innis et al., eds., Academic Press, Inc., New York (1990), pages 13–20). Synthetic amplification products are prepared using the synthetic oligonucleotides of the invention in amplification systems such as PCR (see, e.g., U.S. Pat. No. 4,965,188 to Mullis et al. (Oct. 23, 1990); Scharf, S. J., Chapter 11 in *PCR Protocols: A Guide to Methods and Applications*, Innis et al., eds., Academic Press, Inc., New York (1990), pages 84–98; Chapter 15 in *Current Protocols in Molecular Biology*, Vol. 2, Ausubel et al., eds., John Wiley & Sons, Inc., Boston, Mass. (1994), pages 15.0.1–15.8.8; and Chapter 14 in Sambrook et al., *Molecular Cloning: A Laboratory Manual*, Vol. 2, 2d. Ed., Cold Spring Harbor Laboratory Press, Cold Spring Harbor, N.Y. (1989), pages 14.1–14.35). Those of skill in the art will appreciate that chemical derivatives of nucleotide structures can be substituted for natural nucleotides in the nucleic acids of the invention.

Methods of nucleic acid expression: In one aspect of this embodiment of the invention, the nucleic acids of the invention are used to prepare ARF-p19 proteins, or fusion proteins derived from ARF-p19, via recombinant DNA technology. By inserting any of the nucleic acids of the invention that encode ARF-p19 polypeptide sequences into an appropriate expression vector, and introducing the resultant expression vector construct into appropriate host cells, those skilled in the art can produce large quantities of ARF-p19 polypeptides.

There are numerous host/expression vector systems available for the generation of proteins from the isolated nucleic acids of the invention. These include, but are not limited to, bacteria/plasmid systems, bacteria/phage systems, eukaryotic cell/plasmid systems, eukaryotic cell/virus systems, and the like (see, for example, U.S. Pat. No. 4,440,859 to Rutter et al. (Apr. 3, 1984); Chapter 16 in *Current Protocols in Molecular Biology*, Vol. 2, Ausubel et al., eds., John Wiley & Sons, Inc., Boston, Mass. (1994), pages 16.0.5–16.20.16; and Sambrook et al., *Molecular Cloning: A Laboratory Manual*, Vol. 3, 2d. Ed., Cold Spring Harbor Laboratory Press, Cold Spring Harbor, N.Y. (1989)). One skilled in the art can readily adapt the nucleic acids of the invention to any host/expression vector system which is capable of propagating and expressing heterologous nucleic acids to produce the proteins or polypeptides of the invention. Preferred host/expression systems include bacteria/plasmid systems and insect cell/baculoviral expression vector systems.

Diagnostic methods and kits: In another aspect of this embodiment, ARF-p19 nucleic acid sequences are used to prepare oligonucleotide probes, or PCR primers, to serve as materials for diagnostic tests for ARF-p19 expression, mutation, or deletion in samples of cells isolated from mammals. Deletions of the genes encoding p15 and p16 occur frequently in cancer cells, and the resulting loss of their anti-proliferative functions can contribute to tumorigenesis (Noburi et al., *Nature* 368:753–756 (1994)). Similarly, point mutations, deletions or other mutations in the genes encoding ARF-p19 are diagnostic of cancer or indicative of a predisposition to develop certain types of cancers.

Mutations in the human gene for ARF-p19 are detected by any of a variety of methods depending in part on the nature of the mutation of interest. Deletions and insertions of about 100 base pairs (bp) or more are detected by electrophoretic separation of genomic DNA and hybridization analysis using nucleic acid probes derived from unique portions of the nucleotide sequence of the human ARF-p19 coding sequence (SEQ ID NO:3; see also FIG. 7), or by PCR of genomic DNA using synthetic oligonucleotides derived from the unique portions of the nucleotide sequence of the human ARF-p19 coding sequence as primers. The term "the unique portions of the nucleotide sequence of human ARF-p19" is intended to encompass nucleotide sequences that occur in molecules encoding ARF-p19 but which are not found in p16-InK4a mRNAs.

In one aspect, the invention comprises methods of detecting the presence of a nucleic acid polymorphism associated with a predisposition to develop cancer by analyzing DNA or RNA from a mammal using nucleic acid molecules containing part or all of the unique portions of the nucleotide sequences from an ARF-p19 gene from a mammal, such as a mouse or a human, or the reverse complement thereof. Such methods are used in conjunction with any procedure which will detect the nucleic acids of the invention. Examples of such procedures include hybridization analysis using the nucleic acids of the invention, i.e., isolation of nucleic acids from the cells of a mammal, followed by restriction digestion, separation by a means such as gel electrophoresis, transfer to nitrocellulose or a comparable material, and detection of ARF-p19 nucleic acid sequences thereon by exposure to detectably labeled nucleic acid probes which contain nucleotide sequences encoding ARF-hp19 polypeptide sequences.

In one embodiment of the present invention, the preferred method of detecting the presence of a DNA polymorphism associated with a predisposition to develop cancer involves RFLP (restriction-fragment length polymorphism) techniques based on amplification of ARF-p19 sequences via PCR, followed by restriction digestion and agarose gel electrophoresis. In this method, a biological sample containing nucleated cells, preferably leukocytes, is obtained from a human. Suitable biological samples having nucleated cells that may be used in this invention include, but are not limited to, blood and tissue. The method of obtaining the biological sample will vary depending upon the nature of the sample. By the term "nucleated cells" is meant any cell containing a nucleus. Examples of such cells include, but are not limited to, white blood cells, epithelial cells, or mesenchymal cells. The cells are then isolated from the sample and the DNA from the nucleated cells is purified using conventional methods known in the art such as phenol-chloroform extraction, lytic enzymes, chemical solutions and centrifugation, or size exclusion chromatography (see, for example, Blin and Stafford, *Nucl. Acid Res.* 3:2303–2308 (1976); Maniatis, *Molecular Cloning: A Laboratory Manual*, Cold Spring Harbor Laboratory, Cold Spring Harbor, N.Y. (1982)). Following isolation, the DNA sequences of interest are amplified using conventional PCR methods (see, for example, Innis et at., *PCR Protocols*, Academic Press, N.Y. (1990); Mullis et al., *Cold Spring Harbor Symp. Quant. Biol.* 51:263–273 (1986); Mullis and Faloona, *Methods Enzymol.* 155:335–350 (1987); and Mullis et al., U.S. Pat. No. 4,965,188 (Oct. 23, 1990)).

In one aspect of this embodiment, sequences comprising the unique portions of nucleotide sequences for ARF-p19 are utilized as primers for specific amplification of ARF-p19 nucleic acids (see Example 2). In such an embodiment the amplified product is subjected to restriction digestion prior to visualization. Different alleles of ARF-INK4a will yield amplified fragments of differing size after digestion with an appropriate restriction endonuclease.

The amplified DNA is then precipitated, and digested with a restriction enzyme, such as BamHI, BgII, PstI, or EcoRI. Digested DNA fragments are separated according to their molecular weights to form a pattern, typically using agarose gel electrophoresis. Following electrophoresis, the gel is stained with an appropriate agent, such as ethidium bromide, using standard protocols, and photographed under ultraviolet transillumination. Polymorphisms result in the appearance of additional bands (i.e., bands not found in the wild-type ARF-InK4a allele) on the gel.

In an alternative aspect of this embodiment, the DNA isolated from the cells' nuclei is digested with a given restriction endonuclease, utilizing PCR amplification. The restriction endonucleases that may be used in this invention include, but are not limited to, BamHI, BgM, PstI, or EcoRi. After a digest is obtained, and the DNA is separated by standard technique, for example by agarose gel electrophoresis, the separated bands are probed with one or more DNA fragments containing a unique portion of the nucleotide sequences encoding human ARF-p19 polypeptide sequences. In one aspect of this embodiment, the preferred probe of the invention is based on the cDNA or genomic sequence from the gene for human ARF-p19.

The use of RFLP technology is only one preferred embodiment of detecting polymorphisms in the nucleic acids of the invention. Since, ultimately, the use of RFLP depends on polymorphism in DNA restriction sites along the nucleic acid molecule, other methods of detecting the polymorphism can also be used. Any method of analysis which allows one skilled in the art to determine the linkage between the polymorphism detected by the probes and primers of the present invention can be utilized. Techniques such as direct location of a polymorphism affecting ARF-p19 at its chromosomal location by in situ hybridization (e.g., FISH) using radiolabeled, fluorescence-labeled, or enzyme-labeled probes may be employed. Other suitable techniques include, but are not limited to, amplification methods such as the ribonuclease mis-match cleavage assay and direct oligonucleotide hybridization.

Any size fragment of the human InK4A gene (SEQ ID NO:3) can be utilized as a probe as long as it is capable of hybridizing to a restriction fragment which displays a polymorphism within an intron or an exon required for ARF-p19 expression. The hybridization probes can be labeled by standard labeling techniques such as with a radiolabel, enzyme label, fluorescent label, biotin-avidin label, chemiluminescence, and the like. After hybridization, the probes are visualized using known methods. Comparison of the RFLP or RFLP's for the subject under investigation will quickly reveal the presence or absence of polymorphisms in the gene encoding human ARF-p19 linked to a predisposition to cancer. Polymorphisms that may be detected by the methods of the invention include RFLPs, point mutations, insertions, deletions, inversions, alternately spliced mRNAs, and the like.

The materials for use in this aspect of the invention are ideally suited for the preparation of a kit. Specifically, the invention provides a compartmentalized kit to receive in close confinement, one or more containers which comprises: (a) a first container comprising one or more of the probes or amplification primers of the present invention; and (b) one or more other containers comprising one or more of the following: a sample reservoir, wash reagents, reagents capable of detecting presence of bound probe from the first container, or reagents capable of amplifying sequences hybridizing to the amplification primers.

In detail, a compartmentalized kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (Tris-buffers, etc.), and containers which contain the reagents used to detect the bound probe or amplified product.

Types of detection reagents include labeled secondary probes, or in the alternative, if the primary probe is labeled, the enzymatic, or antibody binding reagents which are capable of reacting with the labeled probe. One skilled in the art will readily recognize that the disclosed probes and amplification primers of the present invention can readily be incorporated into one of the established kit formats which are well known in the art. In one example, a first container may contain a hybridization probe. The second container may contain the restriction enzyme to be used in the digest. Other containers may contain reagents useful in the localization of labeled probes, such as enzyme substrates such as x-gal tagged avidin if a biotinylated probe is utilized. Still other containers may contain buffers, etc.

Gene therapy: In another embodiment of this invention, ARF-p19 nucleic acid sequences are used for gene therapy, i.e., to inhibit, enhance or restore expression of ARF-p19 in cells with reduced, altered or no ARF-p19 activity, using the nucleic acid sequences of the invention.

1. In order to enhance or restore ARF-p19 activity to cells in need of growth regulation, ARF-p19 expression constructs are prepared. An expression construct consists of nucleic acid sequences encoding a protein having ARF-p19 polypeptide sequences operably linked to nucleic acid sequences required for genetic expression in a cell (such as promoters) in an expression vector. The expression constructs are introduced into cells, wherein they direct expression of proteins having ARF-p19 polypeptide sequences. The expressed proteins may be fusion proteins that additionally include polypeptide sequences designed to improve the in vivo activity, targeting and/or stability of the gene products expressed by the expression construct.

The expressed proteins function to restore or enhance ARF-p19 function in their host cells and thus negatively regulate the progression of the cell through the cell cycle. The disclosure demonstrates that, even in cells genetically engineered to overexpress cyclin D and thus possessing 5–10 fold greater levels of CDKs than corresponding wild-type cells, the constitutive expression of ARF-p19 in a cell results in G1 or G2 phase arrest (see Example 5). Thus, even in cells with runaway cyclin D expression, the introduction of ARF-p19 function in excess inhibits the progression of the cells through the cell cycle and thus prevents their further growth.

2. In order to inhibit ARF-p19 activity in cells in need of growth stimulation, synthetic antisense oligonucleotides are prepared from the coding sequences for ARF-p19 found in cDNA clones. An antisense oligonucleotide consists of nucleic acid sequences corresponding to the reverse complements of ARF-p19 coding sequences or other sequences required to be present in ARF-p19 mRNA molecules for in vivo expression. The antisense oligonucleotides are introduced into cells, wherein they specifically bind to ARF-p19 MRNA molecules (and thus inhibit translation of ARF-p19 gene products), or to double-stranded DNA molecules to form triplexes (see U.S. Pat. No. 5,190,931 to Inouye (Mar. 2, 1993); Riordan and Martin, *Nature* 350:442443 (1991)).

Because antisense oligonucleotides bind with high specificity to their targets, selectivity is high and toxic side effects resulting from misdirection of the compounds are minimal, particularly given the present state of the art with regard to the design of, preparation and chemical modification of, and means of delivery to cells for, oligonucleotides (see, e.g., Wagner, R. W., *Nature* 372:333–335 (1994); Tseng and Brown, *Cancer Gene Therapy* 1:65–71 (1994); Morishita, R., et al., *J. Clin. Invest.* 93:1458–1464 (1994); Stein and Cheng, *Science* 261:1004–1012 (1993); Lisziewicz, J., et al., *Proc. Natl. Acad. Sci.* (*USA*) 90:3860–3864 (1993); Watson, P. H., et al., *Cancer Res.* 51:3996–4000 (1991); Han, L., et al., *Proc. Natl. Acad. Sci.* (*USA*) 88:4313–4317 (1991); Florini and Ewton, *J. Biol. Chem.* 265:13435–13437 (1990); and Ullmarm and Peyman, *Chem. Reviews* 90:543–583 (1990)). Means for the delivery of oligonucleotides to cells include, but are not limited to, liposomes (see, e.g., Renneisen, K., et al., *J. Biol. Chem.* 265:16337–16342 (1990)) and introduction of expression constructs that direct the transcription of antisense oligoribonucleotides in vivo (see, e.g., Shohat, O., et al., *Oncogene* 1:277–283 (1987)).

Polypeptides and Related Embodiments

In one embodiment, the invention comprises proteins having amino acid sequences of mouse ARF-p19 protein, human ARF-p19 protein and ARF-p19 polypeptides from other mammals. For example, the invention provides the complete amino acid sequences of mouse ARF-p19 (SEQ ID NO:2) and of human ARF-p19 (SEQ ID NO:4). When introduced into mammalian cells ARF-p19 proteins induce cell cycle arrest or, at lower concentrations, slow cell growth to a desired rate.

One skilled in the art can readily adapt the amino acid sequences of the invention to a variety of known applications. For example, fusion proteins that comprise amino acid sequences from ARF-p19 and a second polypeptide can be produced by recombinant DNA technology to generate novel proteins having properties of both parent proteins (see Example 4). Similarly, the proteins of the invention can be conjugated to other proteins in order to target the conjugated protein to CDK-cyclin complexes in a cell. Synthetic oligopeptides (a.k.a. "peptides") generally contain from about 5 to about 100 contiguous amino acids exactly corresponding to the polypeptide sequence of ARF-p19 of the invention, but may optionally contain additional amino acids at the carboxyl terminus, the amino terminus, or both. Moreover, those of skill in the art will appreciate that substitution of endogenous amino acids for chemical derivatives and/or isomers of amino acids will yield peptides with properties that are enhanced relative to the native ARF-p19 proteins. Properties that may be so altered include, for example, in vivo stability.

Antibodies and Related Embodiments

In another embodiment of the invention, ARF-p19 proteins, or oligopeptide sequences derived therefrom, are used to create antibody compositions that specifically recognize (bind) ARF-p19 epitopes. Antibodies to ARF-p19 serve as probes for diagnostic tests for ARF-p19 expression or as diagnostic materials. Antibodies to ARF-p19 can also be conjugated to toxins to generate specific immunotoxins for use in mammalian therapy.

Methods of generating antibodies using purified proteins or synthetic oligopeptides are known in the art (see *Antibodies: A Laboratory Manual*, Harlow, E., and Lane, D., Cold Spring Harbor Laboratory, Cold Spring Harbor, N.Y. (1988)). The antibody compositions of the invention may be polyclonal, monospecific or monoclonal.

Diagnostic methods and kits: In one aspect of this embodiment, the concentration of ARF-p19 protein in a sample of cells from a mammal is determined by contacting the sample with a detectably labeled antibody composition specific to ARF-p19, qualitatively or quantitatively determining the amount of label bound or not bound in the sample, and calculating therefrom the concentration of ARF-p19 in the sample. The sample of cells is obtained from a mammal and are washed in an appropriate buffer such as Hank's balanced salt solution. The cells are lysed and incubated with a detectably labeled ARF-p19-specific antibody composition for an appropriate amount of time. The cells are washed with the buffer a second time to remove unbound antibody. The amount of bound or unbound labeled antibody is then detected by conventional means.

Alternatively, unlabeled ARF-p19-specific antibody compositions, bound or unbound in a sample, are detected using a secondary antibody or protein which is specific for an immunoglobulin, e.g., protein A, protein G, anti-IgM or anti-IgG antibodies. In this alternative embodiment, the secondary (anti-immunoglobulin) antibodies, which may be monoclonal or polyclonal, are detectably labeled and are detected in the course of carrying out the method.

Alternatively, ARF-p19 levels in a sample of mammalian cells are determined by detecting the level of soluble ARF-p19 in a sample of lysed cells. In this aspect, a sample of lysed cells obtained from a mammal is contacted with an ARF-p19-specific antibody composition which is immobilized onto a solid matrix, and allowed to incubate so as to form an ARF-p19/ARF-p19-specific antibody complex. Following a wash step with suitable buffers to remove the unbound antibody, a detectably labeled molecule which binds to the ARF-p19-specific antibody composition is added. The amount of bound label then is detected to determine the concentration of ARF-p19 present in the sample. Suitable types of immunoassays for detecting ARF-p19 include sandwich immunoassay and competition assays, performed using conventional methods. Naturally, other ligands specific for ARF-p19 may be used in lieu of ARF-p19-specific antibody compositions.

Of course, the specific amounts of ARF-p19-specific antibody compositions and detectably labeled second antibodies, the temperature and time of incubation, as well as other assay conditions may be varied, depending on various factors including the concentration of ARF-p19 in the sample, the nature of the sample, and the like. Those skilled in the art will be able to determine operative and optimal assay conditions for each determination by employing routine experimentation. Other such steps as washing, stirring, shaking, filtering and the like may be added to the assays as is customary or necessary for the particular situation.

A variety of means may be used to detectably label antibody compositions for use in the methods of the invention. For example, one means by which an ARF-p19-specific antibody composition, or secondary antibodies, can be detectably labeled is by conjugation to an enzyme. The conjugated enzyme, when later exposed to its substrate, will react with the substrate in such a manner as to produce a chemical moiety which can be detected, for example, by spectrophotometric, fluorometric or by visual means. Enzymes which can be used to detectably label antibody compositions include, but are not limited to, malate dehydrogenase, staphylococcal nuclease, delta-v-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase. Antibody compositions may also be labeled with a radioactive isotope which can be determined by such means as the use of a gamma counter or a scintillation counter or by autoradiography. It is also possible to label antibody compositions with a fluorescent compound. When fluorescently labeled antibody is exposed to light of the proper wave length, its presence can then be detected due to the fluorescence of the dye. Among the most commonly used fluorescent labeling compounds are fluorescein isothiocyanate, rhodamine, phycoerythrin, phycocyanin, allophycocyanin, o-phthaldehyde and fluorescamine. Antibodies can also be detectably labeled using fluorescence emitting metals such as $^{152}$Eu, or others of the lanthanide series. These metals can be attached to ARF-p19-specific antibodies using such metal chelating groups as diethylenetriaminepentaacetic acid (DTPA) or ethylenediaminetetraacetic acid (EDTA). Antibodies also can be detectably labeled by coupling to a chemiluminescent compound. The presence of chemiluminescent-tagged antibodies is then determined by detecting the presence of luminescence that arises during the course of a chemical reaction. Examples of particularly useful chemiluminescent labeling compounds are luminol, isoluminol, theromatic acridium ester, imidazole, acridinium salt and oxalate ester. Likewise, a bioluminescent compound may be used to label antibody compositions for use in the methods of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of bound or unbound antibodies may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

In another embodiment of the present invention, kits are provided which contain the necessary reagents to carry out the previously described immunoassays with ARF-p19-specific antibodies, in order to diagnose certain types of cancers, or to detect a predisposition for certain types of cancers, in a mammal.

Specifically, the invention provides a compartmentalized kit to receive, in close confinement, one or more containers which comprises: (a) a first container containing an ARF-p19-specific antibody; and (b) one or more other containers containing one or more of the following: wash reagents, and reagents capable of detecting presence of bound or unbound ARF-p19-specific antibodies.

In detail, a compartmentalized kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody.

Types of detection reagents include detectably labeled secondary antibodies, or in the alternative, if the primary antibody is detectably labeled, the appropriate enzymatic or antibody binding reagents which are capable of reacting with the labeled antibody. One skilled in the art will readily recognize that the disclosed antibodies of the present invention can readily be incorporated into any one of the variety of established kit formats which are well known in the art.

Therapeutics and Related Embodiments

Another embodiment of the invention includes screening for and producing new compounds that inhibit the activity of ARF-p19, to be applied to mammalian cells in need of reduced regulation of their cell cycles, cellular growth, and/or DNA replication. For example, in order to promote cellular growth in, e.g., healing processes, "negative-dominant" (Herskowitz, I., *Nature* 329:219–222 (1987)) ARF-p19 variants are prepared which competitively inhibit endogenous ARF-p19 proteins and thereby reduce ARF-p19 activity within a cell. As another example of a means by which cellular growth may be promoted, antibodies that bind regions of ARF-p19 involved in its biological action are introduced into a cell and prevent endogenous ARF-p19 proteins from functioning, thereby reducing ARF-p19 activity within a cell.

In a related embodiment, proteins, fusion proteins, conjugates, or synthetic oligopeptides having ARF-p19 function can be introduced into eukaryotic cells to arrest their progression from G1 to S phases, or from G2 to M phases, during interphase and thus inhibit growth of undesired cells, e.g., cancer cells (see Example 5). ARF-p19, or derivatives thereof, can be employed in combination with conventional excipients, i.e., pharmaceutically acceptable organic or inorganic carrier substances suitable for parenteral application which do not deleteriously react with the active compound. Suitable pharmaceutically acceptable carriers include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions preferably oily or aqueous solutions, as well as suspensions, emulsions, or implants. Aqueous suspensions may contain substances which increase the viscosity of the suspension and include, for example, sodium carboxymethyl cellulose, sorbitol, and/or dextran. Optionally, the suspension may also contain stabilizers.

The term "therapeutically effective amount," for the purposes of the invention, refers to the amount of ARF-p19 or derivatives thereof which is effective to achieve its intended purpose. While individual needs vary, determination of optimal ranges for effective amounts of ARF-p19 or its derivatives is within the skill of the art. Generally, the dosage required to provide an effective amount of the composition, and which can be adjusted by one of ordinary skill in the art will vary, depending on the age, health, physical condition, weight, extent of disease of the recipient, frequency of treatment and the nature and scope of the desired effect.

Transgenic Animals and Related Embodiments

In another embodiment of the invention, ARF-p19 nucleic acid sequences can be used to create transgenic non-human animals to serve as animal models for ARF-p19 overexpression (transgenic expression) or mutations such as multiple stop codons ("knockouts" or "null alleles") or other mutations which alter one or more ARF-p19 activities without affecting InK4a-p16 activity. For example, transgenic mice having little or no ARF-p19 activity due to mutations in one or both alleles of the gene encoding ARF-p19 (INK4A) are prone to develop certain types of tumors.

The non-human animals of the invention comprise any animal having a deficiency of ARF-p19 activity as a result of the transgenic alteration of the gene(s) encoding ARF-p19. Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by nonnatural means (i.e., by human manipulation), one or more genes that do not occur naturally in the animal, e.g., foreign genes, genetically engineered endogenous genes, etc. The nonnaturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. (Watson, J. D., et al., in *Recombinant DNA*, 2d Ed., W. H. Freeman & Co., New York (1992), pages 255–272; Gordon, J. W., *Intl. Rev. Cytol.* 115:171–229 (1989); Jaenisch, R., *Science* 240:1468–1474 (1989); Rossant, J., *Neuron* 2:323–334 (1990)).

Methods of preparing transgenic animals: In one aspect of this embodiment of the invention, the nucleic acids of the invention are used to prepare transgenic constructs to be introduced into non-human animals in order to generate the transgenic animals of the invention. Specifically, ARF-p19 sequences derived from the genome of the non-human animal of choice are used to create such transgenic constructs.

The transgenic non-human animals of the invention are produced by introducing ARF-p19 transgenic constructs into the germline of the non-human animal. Embryonic target cells at various developmental stages are used to introduce the transgenes of the invention. Different methods are used depending on the stage of development of the embryonic target cell(s).

1. Microinjection of zygotes is the preferred method for incorporating transgenes into animal genomes in the course of practicing the invention. A zygote, a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1–2 picoliters of a solution containing transgenic DNA sequences. The use of a zygote for introduction of transgenes has the advantage that, in most cases, the injected transgenic DNA sequences will be incorporated into the host animal's genome before the first cell division (Brinster, et al., *Proc. Natl. Acad. Sci.* (*USA*) 82:4438–442 (1985)). As a consequence, all cells of the resultant transgenic animals (founder animals) stably carry an incorporated transgene at a particular genetic locus, referred to as a transgenic allele. The transgenic allele demonstrates Mendelian inheritance: half of the offspring resulting from the cross of a transgenic animal with a non-transgenic animal will inherit the transgenic allele, in accordance with Mendel's rules of random assortment.

2. Viral integration can also be used to introduce the transgenes of the invention into an animal. The developing embryos are cultured in vitro to the developmental stage known as a blastocyte. At this time, the blastomeres may be infected with appropriate retroviruses (Jaenich, R., *Proc. Natl. Sci.* (*USA*) 73:1260–1264). Infection of the blastomeres is enhanced by enzymatic removal of the zona pellucida (Hogan, et al., in *Manipulating the Mouse Embryo*, Cold Spring Harbor Press, Cold Spring Harbor, N.Y. (1986)). Transgenes are introduced via viral vectors which are typically replication-defective but which remain competent for integration of viral-associated DNA sequences, including transgenic DNA sequences linked to such viral sequences, into the host animal's genome (Jahner, et al., *Proc. Natl. Acad. Sci.* (*USA*) 82:6927–6931 (1985); Van der Putten, et al., *Proc. Natl. Acad. Sci.* (*USA*) 82:6148–6152 (1985)). Transfection is easily and efficiently obtained by culture of blastomeres on a mono-layer of cells producing the transgene-containing viral vector (Van der Putten, et al., *Proc. Natl. Acad. Sci.* (*USA*) 82:6148–6152 (1985); Stewart, et al., *EMBO Journal* 6:383–388 (1987)). Alternatively, infection may be performed at a later stage, such as a blastocoele (Jahner, D., et al., *Nature* 298:623–628 (1982)). In any event, most transgenic founder animals produced by viral integration will be mosaics for the transgenic allele; that is, the transgene is incorporated into only a subset of all the cells that form the transgenic founder animal. Moreover, multiple viral integration events may occur in a single founder animal, generating multiple transgenic alleles which will segregate in future generations of offspring. Introduction of transgenes into germline cells by this method is possible but probably occurs at a low frequency (Jahner, D., et al., *Nature* 298:623–628 (1982)). However, once a transgene has been introduced into germline cells by this method, offspring may be produced in which the transgenic allele is present in all of the animal's cells, i.e., in both somatic and germline cells.

3. Embryonic stem (ES) cells can also serve as target cells for introduction of the transgenes of the invention into animals. ES cells are obtained from pre-implantation embryos that are cultured in vitro (Evans, M. J., et al., *Nature* 292:154–156 (1981); Bradley, M. O., et al., *Nature* 309:255–258 (1984); Gossler, et al., *Proc. Natl. Acad. Sci.* (*USA*) 83:9065–9069 (1986); Robertson et al., *Nature* 322:445–448 (1986); Robertson, E. J., in *Teratocarcinomas and Embryonic Stem Cells: A Practical Approach*, Robertson, E. J., ed., IRL Press, Oxford (1987), pages 71–112). ES cells, which are commercially available (from, e.g., Genome Systems, Inc., St. Louis, Mo.), can be transformed with one or more transgenes by established methods (Lovell-Badge, R. H., in *Teratocarcinomas and Embryonic Stem Cells: A Practical Approach*, Robertson, E. J., ed., IRL Press, Oxford (1987), pages 153–182). Transformed ES cells can be combined with an animal blastocyst, whereafter the ES cells colonize the embryo and contribute to the germline of the resulting animal, which is a chimera (composed of cells derived from two or more animals) (Jaenisch, R., *Science* 240:1468–1474 (1988); Bradley, A., in *Teratocarcinomas and Embryonic Stem Cells: A Practical Approach*, Robertson, E. J., ed., IRL Press, Oxford (1987), pages 113–151). Again, once a transgene has been introduced into germline cells by this method, offspring may be produced in which the transgenic allele is present in all of the animal's cells, i.e., in both somatic and germline cells.

However it occurs, the initial introduction of a transgene is a Lamarckian (non-Mendelian) event. However, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

Transgenes may be introduced into animals in order to provide animal models for human diseases. Transgenes that result in such animal models include, e.g., transgenes that encode mutant gene products associated with an inborn error of metabolism in a human genetic disease and transgenes that encode a human factor required to confer susceptibility to a human pathogen (i.e., a bacterium, virus, or other pathogenic microorganism) (Leder et al., U.S. Pat. No. 5,175,383 (Dec. 29, 1992); Kindt et al., U.S. Pat. No. 5,183,949 (Feb. 2, 1993); Small et al., *Cell* 46:13–18 (1986); Hooper et al., *Nature* 326:292–295 (1987); Stacey et al., *Nature* 332:131–136 (1988); Windle et al., *Nature* 343:665–669 (1990); Katz et al., *Cell* 74:1089–1100 (1993)). Transgenic animals that are predisposed to a disease may be used to identify compositions that induce the disease and to evaluate the pathogenic potential of compositions known or suspected to induce the disease (Berns, A. J. M., U.S. Pat. No. 5,174,986 (Dec. 29, 1992)).

Offspring that have inherited the transgenes of the invention are distinguished from littermates that have not inherited transgenes by analysis of genetic material from the offspring for the presence of biomolecules that comprise unique sequences corresponding to sequences of, or encoded by, the transgenes of the invention. For example, biological fluids that contain polypeptides uniquely encoded by the transgenes of the invention may be immunoassayed for the presence of the polypeptides. A more simple and reliable means of identifying transgenic offspring comprises obtaining a tissue sample from an extremity of an animal, e.g., a tail, and analyzing the sample for the presence of nucleic acid sequences corresponding to the DNA sequence of a unique portion or portions of the transgenes of the invention. The presence of such nucleic acid sequences may be determined by, e.g., hybridization ("Southern") analysis with DNA sequences corresponding to unique portions of the transgene, analysis of the products of PCR reactions using DNA sequences in a sample as substrates and oligonucleotides derived from the transgene's DNA sequence, etc.

Null alleles: A preferred embodiment is a transgenic animal that is homozygous for a null (a.k.a. "knock-out") allele of ARF-INK4A but which has a wild-type INK4A-p16 allele. For example, selective interruption of INK4A exon 1β eliminates ARF-INK4A expression but does not affect sequences encoding InK4a-p16. Additionally or alternatively, one or more point mutations that create stop codons in the ARF-p19 reading frame, but which result in silent mutations in the InK4a-p16 reading frame, are introduced by site-directed mutagenesis into cloned INK4A genomic nucleic acid sequences which are then reintroduced into the genome of an animal to generate a transgenic ARF-p19-deficient animal. The transgenic ARF-p19 null or ARF-p19-deficient animals of the invention are predisposed to develop certain types of cancers, including but not limited to melanomas, in a reproducible and thus reliable manner.

In order to generate null alleles in embryonic stem cells, the positive-negative selection strategy of Mansour et al. (*Nature* 336:348–352 (1988)) is applied. A positive selectable marker, for example the hygromycin phosphotransferase cassette (van Deursen and Wieringa, *Nucl. Acids Res.* 29:3815–3820 (1992)), is inserted into a 5' portion of an INK4 gene. This position for the positive selectable marker is chosen to obtain a genuine null mutant allele, i.e., to avoid translation of a truncated polypeptide. In the resulting targeting vector the hygromycin gene is flanked 5' and 3' by several kb of homologous murine genomic sequences. In addition, a negative selectable marker, for example the Herpes Simplex Virus (HSV) thymidine kinase (PK) gene, is placed in a 3' position flanking the region of homologous sequences in order to enable selection against nonhomologous integrants. Both the positive and negative selectable markers are inserted in the antisense orientation with respect to the transcriptional orientation of the Ink4 gene, and are expressed due to the TK promoter and Py F441 Polyoma enhancer. Linearized targeting construct is introduced into ES cells by electroporation or other suitable means and selection with hygromycin and FIAU (1-[2-deoxy, 2-fluoro-β-D-arabinofuranosyl]) is carried out for 7 to 10 days. Resistant colonies are expanded in 24-well plates; half of the cells in each well are cryo-preserved and the other half expanded for genotype analysis. Positive clones are stored in liquid nitrogen and thawed at least 3 days prior to blastocyst injection. Blastocysts are isolated, for example, at day 3.5 postcoitum by flushing the uterine horns of naturally mated C57BL/6 pregnant females with DMEM+10% FBS. Approximately 10 to 15 ES cells from each homologous recombinant clone with a normal karyotype are microinjected into recipient blastocysts, and about 10 to 20 embryos are transferred into the uterine horns of (C57BL/6×CBA/Ca) F1 pseudopregnant fosters (Bradley, A., in *Teratocarcinomas and Embryonic Stem Cells: A Practical Approach*, Robertson, E. J., ed., IRL Press, Oxford (1987), pages 113–151). Chimeric males are mated with C57BL/6 or FVB/J females and germline transmission of the mutant allele is verified by Southern blot analysis of tail DNA from F1 offspring with either agouti or gray coat color. F2 offspring from interbred heterozygotes are genotyped by Southern blotting to identify homozygous null mutants.

Methods of evaluating the therapeutic or oncogenic potential of compositions: Using the transgenic animals of the invention, it is possible to evaluate a variety of compositions for their therapeutic or oncogenic potential.

1. Generally, methods for determining the therapeutic potential of a composition to treat cancer comprise the step of administering a known dose of the composition to a transgenic animal having a phenotype of reduced or altered ARF-p19 activity, monitoring resulting biological or biochemical parameters correlated with cancer, and comparing the symptoms of treated animals to those of untreated animals.

A first method of assessing the therapeutic potential of a composition using the transgenic animals of the invention comprises the steps of:

(1) Administering a known dose of the composition to a first transgenic animal having a phenotype of reduced or altered ARF-p19 activity;

(2) Detecting the time of onset of cancer in the first transgenic animal; and (3) Comparing the time of onset of cancer in the first transgenic animal to the time of onset of cancer in a second transgenic animal having a phenotype of reduced or altered ARF-p19 activity, which has not been exposed to the composition, wherein a statistically significant decrease in the time of onset of cancer in the first transgenic animal relative to the time of onset of the symptoms in the second transgenic animal indicates the therapeutic potential of the composition for treating cancer.

A second method of assessing the therapeutic potential of a composition using the transgenic animals of the invention comprises the steps of:

(1) Administering a known dose of the composition to a first transgenic animal having a phenotype of reduced or altered ARF-p19 activity, at an initial time, $t_0$;

(2) Determining the extent of cancer in the first transgenic animal at a later time, $t_1$; and (3) Comparing, at $t_1$, the extent of cancer in the first transgenic animal to the extent of neurological symptoms in a second transgenic animal having a phenotype of reduced or altered ARF-p19 activity, which has not been exposed to the composition at $t_0$, wherein a statistically significant decrease in the extent of cancer at $t_1$ in the first transgenic animal relative to the extent of the symptoms at $t_1$ in the second transgenic animal indicates the therapeutic potential of the composition for treating cancer.

A third method of assessing the therapeutic potential of a composition using the transgenic animals of the invention comprises the steps of:

(1) Administering a known dose of the composition to a first transgenic animal having a phenotype of reduced or altered ARF-p19 activity;

(2) Measuring the lifespan of the first trarsgenic animal; and (3) Comparing the lifespan of the first transgenic animal to the lifespan of a second transgenic animal having a phenotype of reduced or altered ARF-p19 activity, which has not been exposed to the composition, wherein a statistically significant increase in the lifespan of the first transgenic animal relative to the lifespan of the second transgenic animal indicates the therapeutic potential of the composition for treating cancer.

2. Generally, methods for determining the potential of a composition to cause or exacerbate cancer comprise the step of administering a known dose of the composition to a transgenic animals having a phenotype of reduced or altered ARF-p19 activity, monitoring resulting biological or biochemical parameters correlated with cancer, and comparing the symptoms of treated animals to those of untreated animals.

A first method of assessing the oncogenic potential of a composition using the transgenic animals of the invention comprises the steps of:

(1) Administering a known dose of the composition to a first transgenic animal having a phenotype of reduced or altered ARF-p19 activity;

(2) Detecting the time of onset of cancer in the first transgenic animal; and (3) Comparing the time of onset of cancer in the first transgenic animal to the time of onset of cancer in a second transgenic animal having a phenotype of reduced or altered ARF-p19 activity, which has not been exposed to the composition, wherein a statistically significant increase in the time of onset of cancer in the first transgenic animal relative to the time of onset of the symptoms in the second transgenic animal indicates the potential of the composition for causing or exacerbating cancer.

A second method of assessing the oncogenic potential of a composition using the transgenic animals of the invention comprises the steps of:

(1) Administering a known dose of the composition to a first transgenic animal having a phenotype of reduced or altered ARF-p19 activity, at an initial time, $t_0$;

(2) Determining the extent of cancer in the first transgenic animal at a later time, $t_1$; and (3) Comparing, at $t_1$, the extent of cancer in the first transgenic animal to the extent of neurological symptoms in a second transgenic animal having a phenotype of reduced or altered ARF-p19 activity, which has not been exposed to the composition at $t_0$, wherein a statistically significant increase in the extent of cancer at $t_1$ in the first transgenic animal relative to the extent of the symptoms at $t_1$ in the second transgenic animal indicates the potential of the composition for causing or exacerbating cancer.

A third method of assessing the oncogenic potential of a composition using the transgenic animals of the invention comprises the steps of:

(1) Administering a known dose of the composition to a first transgenic animal having a phenotype of reduced or altered ARF-p19 activity;

(2) Measuring the lifespan of the first transgenic animal; and (3) Comparing the lifespan of the first transgenic animal to the lifespan of a second transgenic animal having a phenotype of reduced or altered ARF-p19 activity, which has not been exposed to the composition, wherein a statistically significant decrease in the lifespan of the first transgenic animal relative to the lifespan of the second transgenic animal indicates the potential of the composition for causing or exacerbating cancer.

In both of the above sets of methods, the composition may comprise a chemical compound administered by circulatory injection or oral ingestion. The composition being evaluated may alternatively comprise a polypeptide administered by circulatory injection of an isolated or recombinant bacterium or virus that is live or attenuated, wherein the polypeptide is present on the surface of the bacterium or virus prior to injection, or a polypeptide administered by circulatory injection of an isolated or recombinant bacterium or virus capable of reproduction within a mouse, and the polypeptide is produced within a mouse by genetic expression of a DNA sequence encoding the polypeptide. Alternatively, the composition being evaluated may comprise one or more nucleic acids, including a gene from the human genome or a processed RNA transcript thereof.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

The entire text of all publications cited above and below are hereby incorporated by reference.

EXAMPLES

Example 1
cDNA Sequences Encoding ARF-p19

Tandemly linked INK4A (MTS1, CDKN2) and INK4B (MTS2) genes on the short arm of human chromosome 9 encode distinct 16 kDa and 15 kDa inhibitors (InK4a-p16 and InK4b-p15, respectively) of the G1 cyclin D-dependent kinases CDK4 and CDK6 (Serrano et al., *Nature* 366:704–707 (1993); Hannon and Beach, *Nature* 371:257–261 (1994)). Homozygous co-deletion of INK4A and INK4B, hemizygous deletions of INK4A together with point mutations within the remaining allele, and de novo methylation of an CpG island extending into exon 1 of INK4A (Merlo et al., *Nature Med.* 7:686–692 (1995)) are commonly observed in human cancers, suggesting that InK4a-p16, and perhaps InK4b-p15, function as tumor suppressors (Kamb, A. et al., *Science* 264:436440 (1994); Noburi, T. et al., *Nature* 368:753–756 (1994); Sheaff and Roberts, *Curr. Biol.* 5:28–31 (1994); Hunter and Pines, Cell 79:573–582 (1995)). Two other members of the IAW4 gene family, InK4c-p18 and INK4d-p19, map to different human chromosomes (Guan et al., *Genes & Develop.* 8:2939–2952 ((1994); Chan et al., *Mol. Cell. Biol.* 15:2682–2688 (1995);

Hirai et al., *Mol. Cell. Biol.* 15:2672–2681 (1995); Okuda et al., *Genomics* (in press) (1995)).

The human INK4A gene yields transcripts that initiate at two promoters, the first (E1α) located in close proximity to other InK4a-p16 coding exons and the second (E1β) mapping centromerically in close proximity to the INK4b gene (Stone, S., et al., *Cancer Res.* 55:2988–2994 (1995); Mao, L., et al., *Cancer Res.* 55:2995–2997 (1995)). A long microsatellite ($CA_N$) repeat downstream of exon 1β is highly polymorphic. The nucleotide sequence of mRNAs derived from exon 1β include a 5' AUG codon which, if used to initiate protein synthesis in fully spliced transcripts, can yield another polypeptide (here designated ARF-p19) derived from a theoretical Alternative Reading Frame that includes most of the exon 2 coding sequences represented in INK4a-p16 mRNA. Two classes of transcripts (α and β, containing 5' sequences derived from exons 1α and 1β, respectively), although virtually identical in length, have been successfully identified by reverse transcription and polymerase chain reactions (RT-PCR) using MRNA templates from a variety of human tissues, but others inferred that the P transcript is unlikely to encode a protein (Stone, S., et al., *Cancer Res.* 55:2988–2994 (1995); Mao, L., et al., *Cancer Res.* 55:2995–2997 (1995)). However, as described herein, mouse exon 1β sequences are spliced to exon 2 of the INK4A gene to generate transcripts encoding a polypeptide that is completely different in amino acid sequence from InK4a-p16.

A mouse erythroleukemia (MEL) cell DNA library (5' Stretch λgt10, Clontech, Palo Alto, Calif.) was screened with a full-length human InK4a-p16 probe, and twelve hybridizing cDNAs subcloned into pBluescript (Stratagene, La Jolla, Calif. were sequenced. One cDNA represented mouse InK4a-p16 (Quelle et al., *Oncogene* 11:635–645 (1995)) while the remaining clones, designated ARF-p19, contained alternative sequences derived from exon 1β (FIG. 1; SEQ ID NO:1). As confirmed by Southern blotting analysis, the unrelated sequences from the 1α and 1β exons hybridized to distinct genomic DNA fragments.

The mouse β MRNA, which directs the expression of ARF-p19 in a variety of tissues (see Examples 2 to 4), contains an AUG codon at nucleotides 43–45 flanked by Kozak consensus sequences, and translation from this initiator would yield a 169 amino acid polypeptide of 19,349 daltons (ARF-p19; SEQ ID NO:2). Splicing of exon 1β to exon 2 of the INK4A gene occurs at the same acceptor site as that used by exon 1β but changes the exon 2 reading frame to generate an entirely novel protein containing 105 exon 2-derived residues. The mouse and human 1β exons are conserved in length, except for one additional arginine codon in the human β MRNA located just 5' of the splice donor site. The reading frame (SEQ ID NO:3; FIG. 7) for the human ARF-p19 protein (SEQ ID NO:4) is only 132 codons in length due to a predicted TGA terminator in place of CCA at nucleotides 436–438 (FIG. 1). Mouse and human ARF-p19 polypeptides are 44% identical through their exon 1β segments and 46% identical overall. By comparison, INK4A exon 1α segments are 72% identical, with mouse and human InK4a-p16 proteins sharing 65% overall identity.

The ARF-p19 proteins are highly basic, as indicated by their high arginine content (human, 21% Arg; mouse 22% Arg) and are unrelated to known proteins in searchable databases. However, several known RNA-binding proteins, while not having amino acid sequences that are per se homologous to that of ARF-p19, nonetheless resemble ARF-p19 by having stretches of arginine-rich sequences. Moreover, in at least some instances, these arginine-rich regions have been implicated in the binding of these proteins to specific RNA sequences (Craven, M. G., et al., *J. Bacteriol.* 176:1394–1404 (1994): Calnan, B. J., et al., *Science* 252:1167–1171 (1991), and erratum, 255:665 (1992)); Lazinski, D., *Cell* 59:207–218 (1989); Tao, J., et al., *Proc. Natl. Acad. Sci. (U.S.A.)* 89:2723–2726 (1992)).

There are precedents for dual utilization of coding sequences in small virus genomes which cannot exceed a complexity that prevents their packaging into virions (Lamb and Horvath, *Trends in Genetics* 7:261–266 (1991); Cullen, *Annu. Rev. Microbiol.* 45:219–250 (1991)). In contrast, eukaryotic genes are composed largely of introns and are more widely spaced, presumably relieving them from evolutionarily imposed size constraints. In *Saccharonryces cerevisiae*, the SNF6 locus and genes encoding certain glycolytic enzymes exhibit overlapping reading frames on opposite strands (Estruch and Carlson, *Mol. Cell. Biol.* 10:2544–2553 (1990); Boles and Zimmermann, *Mol. Ben. Genet.* 243:363–368 (1994)), whereas the stress response gene, DDR48, includes two overlapping but asyntactic reading frames, each with a capacity to encode a protein of ~45 kDa (Treger and McEntee, *Mol. Cell. Biol.* 10:3174–3184 (1990)). In these cases, however, only one of the two asyntactic reading frames appears to be expressed. Recently, Labarriere et al. (*J. Biol. Chem.* 270:19205–19208 (1995)) reported that transcripts originating from a novel promoter in the human growth hormone (GH) gene have the potential to specify a 107 amino acid protein, the C-terminal half of which arises from a second reading frame in GH exons 1 and 2. Antibodies to the C-terminus of this predicted polypeptide histochemically stained a subpopulation of pituitary cells, arguing for limited focal translation of this mRNA. In general, however, overlapping genes noted as such in the available databases have not been assigned dual protein products. That two INK4A-coded polypeptides can each induce cell cycle arrest, albeit at different points in the cycle and via apparently distinct mechanisms (see Example 5), suggests that their unitary inheritance has functional significance.

It is noteworthy that alternative splicing of transcripts from another cell cycle-controlling gene, that encoding integrin $β_1$, produces a second gene product, $β_{1C}$, that also functions to regulate cell cycle arrest (Merdith et al., *Science* 269:1570–1572 (1995)). However, unlike ARF-p19 and InK4a-p16, the integrin $β_1$ and $β_{1C}$ reading frames overlap syntactically rather than a syntactically. Specifically, $β_{1C}$ contains a carboxyl-terminal 48-amino acid sequence that replaces the carboxyl-terminal 21 amino acids found in $β_1$; otherwise, however, the sequences of the two proteins are identical. If alternative splicing of RNA transcripts is a recurring motif of cell cycle gene expression then, conceivably, a limited number of common RNA splicing factors could affect the expression of many proteins involved in the regulation of progression through the cell cycle.

Example 2

ARF-p19 is Expressed in Mouse Cells and Tissues

In a survey of mouse tissues and cells lines α and β mRNAs of similar length (~1 kb) were detected by Northern blotting with specific exon1α and exon 1β probes and, in agreement, by RT-PCR using specific 5' primers (FIG. 2).

For RT-PCR Analysis, polyadenylated MRNA was prepared from tissues excised from normal female mice (C3H/HEJ, Jackson Laboratories, Bar Harbor, Me.), and cDNA was synthesized from 50 ng of polyA MRNA templates according to manufacturer's instructions (StrataScript RT-PCR Kit, Stratagene) (Quelle et al., *Oncogene*

11:635–645 (1995)). PCR amplification of either mouse ARF-p19 β transcripts, or of InK4a-p16α transcripts, was performed using a common antisense primer having the sequence

5'-GCAAAGCTTGAGGCCGGATTTAGCTCTGCT(SEQ ID NO:5 and either an ARF-p19 specific sense primer having the sequence

5'-AGGGATCCTTGGTCACTGTGAGGATTC    SEQ ID NO:6 or an InK4a-p16 specific sense primer having the sequence

5'-CGGGATCCGCTGCAGACAGACTGGCCAG    SEQ ID NO:7 with 35 cycles of denaturation (95° C., 1 min), annealing (65° C., 45 sec), and extension (720° C., 2 min). Products (~0.5 kb, 10 μl per lane) were electrophoresed on 1.5% agarose gels and blotted onto nylon membranes (Hybond N, Amersham, Arlington Heights, Ill.). $^{32}$P-labeled probes which specifically recognized exon 1β (ARF-p19, bases 1–228 of SEQ ID NO:1), exon 1α (InK4a-p16, bases 58–182), or an antisense oligonucleotide derived from exon 2 and having the sequence

5'-CGTCTAGAGCGTGTCCAGGAAGCCTTCC    SEQ ID NO:8 were hybridized at 50° C. in neutral pH buffer containing 0.9M NaCl and washed in 0.015M NaCl, 0.1% SDS at the same temperature.

Figure 2B:
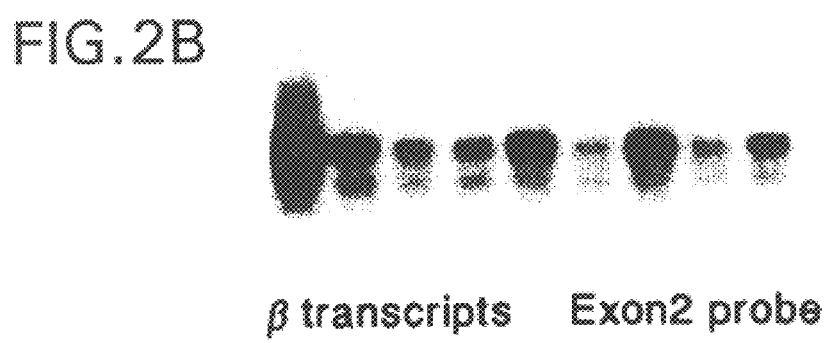
Figure 2C:
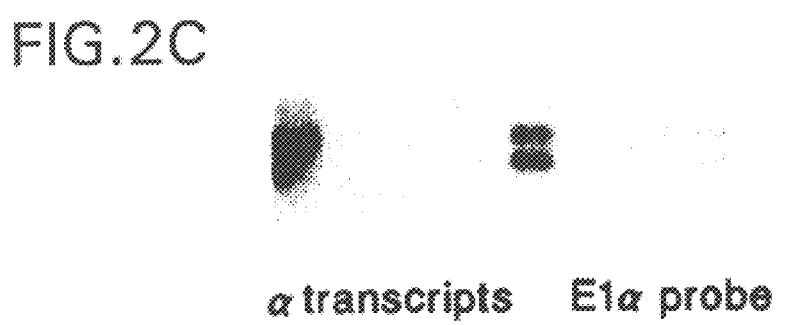
Figure 2D:
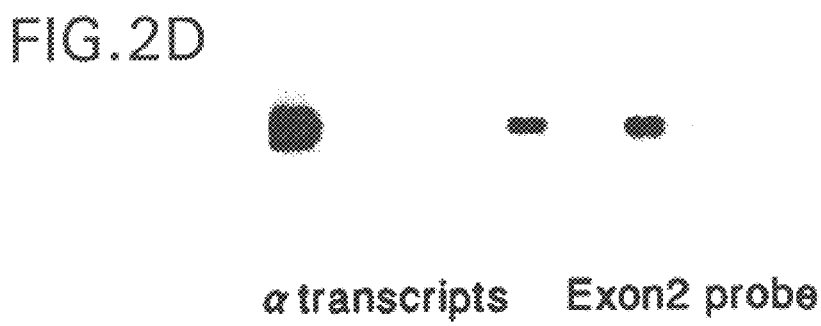

Specific amplification of 0 transcripts and hybridization of the products with exon 1β (FIG. 2(A)) and exon 2 (FIG. 2(B)) probes revealed their ubiquitous expression in various organs. The signal was particularly high using mRNA templates from MEL cells from which both α and β cDNAs have been cloned. By contrast, α mRNAs encoding INK4a-p16 were expressed at relatively high levels in only few tissues (Quelle et al., *Oncogene* 11:635–645 (1995)), and the more restricted patterns of hybridization observed with the exon 1α and exon 2 probes confirmed the specificity of the PCR primers (FIGS. 2(C) and 2(D)). Importantly, amplified a transcripts generated no signal at all after hybridization with the exon 1β probe and vice versa, and no products were obtained in the absence of mRNA templates (FIG. 2). ARF-p19-encoding β transcripts were also detected in other cell lines, including CTLL-2 and RL-12 T cells, and NFS112 B cells, but were absent from. NIH-3T3 fibroblasts and BAC1.2F5 macrophages, both of which have sustained deletions of the INK4A locus (data not shown).

Example 3

Antibodies to ARF-p19 and Detection of ARF-p19 Proteins

An antiserum directed to the unique carboxy-terminal amino acid sequences was generated using a synthetic, conjugated carboxy terminal oligopeptide derived from the ARF-p19 protein using techniques previously described for InK4a-p16-derived oligopeptides (Quelle et al., *Oncogene* 11:635–645 (1995)). Specifically, a synthetic peptide having the sequence (SEQ ID NO:9):

NH$_2$-Val-Phe-Val-Tyr-Arg-Trp-Glu-Arg-Arg-Pro-Asp-Arg-Arg-Ala corresponding to residues 156–169 of murine ARF-p19 protein (SEQ ID NO:2) was used.

The antibody to ARF-p19 carboxy-terminal sequences encoded by the β nRNA precipitated a protein with an apparent molecular mass of about 22 kDa (i.e., AR-p19) after transcription and translation of the β cDNA in vitro (FIG. 3, lane 8). There is no evidence that ARF-p19 undergoes post-translational modification(s) in vivo that detectably alter its mobility on denaturing gels (see Example 4), so the apparent disparity between the masses of the predicted and translated proteins likely reflect the unusual amino acid composition of ARF-p19 (FIG. 1). An antiserum to the C-terminus of mouse InK4a-p16 detected the cognate protein (FIG. 3, lane 6) but did not cross-react with ARF-p19 (FIG. 3, lane 9).

Sequences encoding a hemagglutinin (HA) epitope tag were added to the 5' end of the ARF-p19 cDNA by polymerase chain reaction (P)CR) using a forward primer containing a 5' BamHI site (underlined) having the sequence (SEQ ID NO:10):

5'-CG<u>GGATCCG</u>AATTCAGCCATGGGTTACCATACGACG-
TCCCAGACTACGCTACCGGTCGCAGGTTCTTGGTCAC and a reverse primer extending over the single BssHHI site (underlined) in exon 1β having the sequence of the reverse complement of residues 68–87 of SEQ ID NO:1, i.e., 5'-GCCC<u>GCGCGC</u>TGAATCCTCA    SEQ ID NO:11

The PCR product was digested with BamHI and BssHII, subcloned into the original cDNA in pBluescript, and resequenced. The resultant ARF-p19 fusion protein, in which the amino terminus of ARF-p19 is tagged with a hemagglutinin (HA) epitope, has a mobility that is slightly retarded compared to that of wild-type ARF-p19 (FIG. 3, lane 2). The HA-tagged ARF-p19 protein could be detected with anti-HA serum (see below).

The endogenous ARF-p19 protein could also be detected in lysates of mouse MEL cells (FIG. 4(A), lane 9, arrow), which synthesize high levels of both α and β mRNAs (FIG. 2). Protein InK4a-p16, expressed in MEL cells (FIG. 4(C), lane 9), was not detected with antiserum to ARF-p19, nor vice versa (compare FIGS. 4(A) and 4(C)), confirming the specificity of the antisera and indicating as well that an N-terminally truncated InK4a-p16 protein, which would have carboxylterminal ARF-p19 sequences, does not normally arise by initiation from internal AUG codons within the β mRNA.

Figure 5A:
Figure 5B:
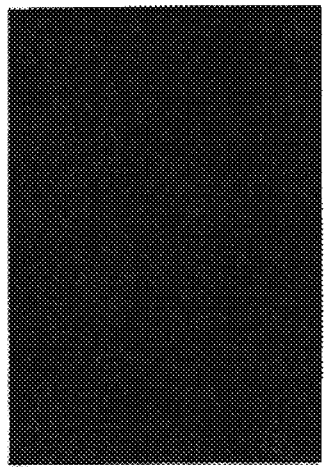
Figure 5C:
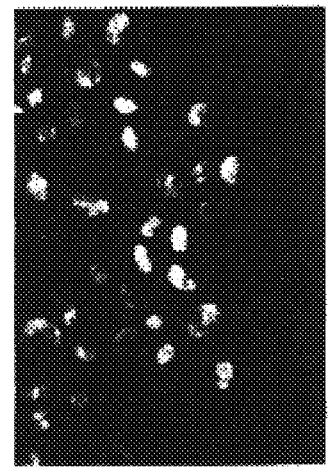

In cytospins prepared from cells harvested 48 hours after infection with viruses encoding HA-tagged ARF-p19, immunofluorescence using detectably labeled antibodies to the ARF-p19 C-terminus (FIG. 5(A)) or to the amino-terminal HA epitope (FIG. 5(C)) demonstrate that both untagged and HA-tagged ARF-p19 localize to the cell nucleus. This reflects the strictly nuclear localization of wild-type ARF-p19, which is normally expressed in derivatives of Balb/c fibroblasts (data not shown).

Example 4

Production of Recombinant ARF-p19 Native and Fusion Proteins

Baculoviral Expression in Insect Sf9 Cells

For expression in insect Sf9 cells (Kato et al., *Genes & Devel.* 7:331–342 (1993)), an EcoRI fragment encoding tagged ARF-p19 was inserted into the pVL1393 baculovirus vector (Pharmingen, San Diego, Calif.). Insect Sf9 cells were infected and harvested as previously described (Kato et al., *Genes & Devel.* 7:331–342 (1993); see also Richardson, C. D., ed., *Baculovirus Expression Protocols*, Methods in Molecular Biology Vol. 39, Walker, J. M., series ed., Humana Press, Totowa, N.J. (1995), Chapters 1–5 and 11).

When the cDNA encoding HA-tagged ARF-p19 was expressed under baculoviral control in insect Sf9 cells, a protein of slightly slower mobility than that of the endogenous protein in MEL cells was detected with antibody to ARF-p19 (FIG. 4(A), lane 2) or to the hemagglutinin (HA) tag (FIG. 4(B), lane 2).

Virus Production and Infection of Mammalian Cells

Both untagged and HA-tagged ARF-p19 cDNAs were subcloned into the EcoRI site of the SRa-MSV-tk-neo retroviral vector (Muller et al., Mol. Cell. Biol. 11:1785–1792 (1994)) for production of virus. Human kidney 293T cells were transfected with 15 μg ecotropic helper virus DNA plus 15 μg SRα vector DNA using a modified calcium phosphate precipitation technique (Chen and Okayama, Mol. Cell. Biol. 7:2745–2752 (1987)). Cell supernatants containing infectious retroviral pseudotypes were harvested 24–60 hours post-transfection, pooled on ice, and filter (0.45μ) sterilized. Virus infections of exponentially growing mouse fibroblasts in 100 mm diameter culture dishes were performed at 37° C. in a 4% $CO_2$ atmosphere using 2 ml virus-containing supernatants containing 8 μg/ml polybrene (Sigma, St. Louis, Mo.). After 3 hours, 10 ml fresh medium was added. Cells were harvested 48 hours after infection and their DNA content was analyzed by flow cytometry (Matsushime et al., Cell 65:701–703 (1991)).

Mammalian cell lines were maintained in Dulbecco's modified Eagle's medium (DMEM) supplemented with 10% fetal bovine serum, 2 mM glutanine, and 100 units/ml penicillin and streptomycin (Gibco, Grand Island, N.Y.). NIH-3T3 cells ($Rb^+$, $INK4A^-$, p53 status uncertain) were transfected with vectors encoding D-type cyclins alone or with CDK4, and polyclonal populations derived from pooled, drug resistant transformants were used (Quelle et al., Genes & Devel. 7:1559–1571 (1993)). Derivatives of Balb-3T3 cells (Rb status uncertain, $INK4a-p16^+$, $p53^-$) were provided by G. Zambetti (St. Jude Children's Research Hospital), and the 293T retrovirus packaging line (Pear et al., Proc. Natl. Acad. Sci. USA 90:8392–8396 (1993)) was obtained from Charles Sawyers (UCLA) with permission from David Baltimore (MIT).

For analysis of ARF-p19 or InK4a-p16 expression, pelleted mammalian cells were disrupted in ice-cold cell lysis buffer (1 x 107 cells/nil) for 1 hour on ice. Nuclei and debris were removed by centrifugation in a microfuge at 12,000 rpm for 10 min at 4° C. Supernatants were boiled in gel loading buffer, and proteins ($2\times10^5$ cell equivalents per lane) were separated on denaturing gels as above and transferred onto nitrocellulose (Quelle et al., Genes & Devel. 7:1559–1571 (1993)). Proteins were detected by enhanced chemiluminescence (ECL, Amershani) according to manufacturer's specifications with ARF-p19 or InK4a-p16 antisera or with 12CA5 monoclonal antibody to the HA tag (ICN, Costa Mesa, Calif.). Assays for CDC2 and CDK2-associated histone H1 kinase activity were performed as previously described (Matsushime et al., Cell 71:323–334 (1992)). In some experiments, specifically immunoprecipitated CDKs or cyclins were separated on denaturing gels and immunoblotted with anti-ARF-p19 as above.

Infection of INK4negative NIH-3T3 cells engineered to overexpress cyclin D1 with a retrovirus containing the β cDNA led to ectopic ARF-p19 synthesis (FIG. 4A, lane 4). When the HA-tagged ARF-p19 protein was introduced, the polypeptide again migrated with a slightly slower mobility than the wild-type protein (FIG. 4A, lane 5 versus 4) and was also revealed with anti-HA serum (FIG. 4B, lane 5). Unlike NIH-3T3 cells which lack the INK4A gene and do not express ARF-p19 (FIG. 4A, lane 3) or InK4a-p16 (FIG. 4C, lanes 3–5), derivatives of Balb-3T3 cells synthesize both proteins (FIGS. 4A and 4C, lanes 7 and 8). Therefore, the β transcript encodes an authentic ARF-p19 protein which is coexpressed with InK4a-p16 in MEL and Balb-3T3derived cell lines.

Example 5
Induction of Cell Cycle Arrest by ARF-p19

In the experiments shown in FIG. 4, the DNA content of cells expressing ARF-p19 was concomitantly measured in order to assess the effect(s) of ARF-p19 on the cell cycle. Surprisingly, infection of NIH-3T3 cells for 48 hours with retroviruses encoding ARF-p19 induced cell cycle arrest in both the G1 (2N DNA content) and G2/M (4N DNA content) phases of the cell cycle with a proportional loss of cells in S phase (DNA content between 2N and 4N) (Table 1). Cells infected with the empty vector were distributed throughout the cycle in a manner indistinguishable from uninfected cells. In similar experiments performed with cells engineered to overexpress cyclin D1, a greater proportion of ARF-p19 expressing cells arrested in G2/M versus G1 (Table 1). Proliferating cyclin D1 overexpressors have a 20–30% contracted G1 phase interval and a compensatory shortening of their doubling time, so that their overall cell cycle distribution is unchanged (Quelle et al., Genes & Devel. 7:1559–1571 (1993)). However, the relative increase in the G2/M versus the G1 phase fraction suggests that cyclin D1 overexpression partially overcomes the p19-induced G1 block.

TABLE 1

Cell Cycle Arrest by ARF-p19

| Cell Line (No. Expts) | Vector cDNA Insert | Cell Cycle Distribution (48 hrs post-infection) | | |
|---|---|---|---|---|
| | | % $G_0G1$ | % S | % G2/M |
| NIH-3T3 (7) | None | 42.4 ± 3.3 | 42.0 ± 2.3 | 15.6 ± 3.3 |
| NIH-3T3 (8) | P19$^{ARF}$ | 66.6 ± 5.2 | 12.5 ± 2.6 | 20.9 ± 5.1 |
| 3T3-D1 (8) | None | 41.1 ± 6.6 | 39.1 ± 4.4 | 19.8 ± 2.7 |
| 3T3-D1 (9) | p19$^{ARF}$ | 53.0 ± 4.3 | 11.6 ± 2.8 | 35.4 ± 4.2 |
| BALB-3T3 (3) | None | 36.5 ± 8.9 | 49.0 ± 8.8 | 14.5 ± 1.2 |
| BALB-3T3(3) | P19$^{ARF}$ | 57.1 ± 4.9 | 26.0 ± 2.8 | 16.9 ± 1.4 |

In these experiments, the DNA content of NIH-3T3 cells infected for 48 hours with a control vector or with retroviruses encoding ARF-p19 was determined by FACS analysis. Proliferating polyclonal derivatives overexpressing cyclin D1 (3T3-D1) are not redistributed through the cell cycle, because the shortening of their G1 phase by 20–30% is compensated by a reduced generation time (Quelle et al., Genes & Devel. 7:1559–1571 (1993)). ARF-p19-induced G2→M arrest in all cyclin D overexpressors was more marked than in parental cells. Arrested cells were fully viable, lacked metaphases, and contained intact nuclei (FIG. 5), features all indicative of arrest in interphase.

Infection of NIH-3T3 or 3T3-D1 overexpressors with retroviruses expressing InK4a-p16 or InK4d-p19 leads only to G1 phase arrest (Hirai et al., Mol. Cell. Biol. 15:2672–2681 (1995); Quelle et al., Oncogene 11:635–645 (1995)). The fact that a significant proportion of cells ectopically expressing ARF-p19 accumulate in G2JM suggests that the action of the ARF-p19 protein is not limited to effects relating to InK4a-p16 activity.

The phenotype of the ARF-p19 expressors was unusual in that many of the infected NIH-3T3 cells appeared rounded and highly refractile, superficially similar to those in mitosis. However, cells enforced to express ARF-p19 exhibited only a minor (<0.2%) metaphase fraction compared to cells infected with the vector control (~3%). Nor did the cells undergo apoptosis, as determined by the following sensitive flow cytometric assay and by their lack of DNA fragmentation.

Apoptosis Assay

Trypsinized cell suspensions were washed and suspended in 0.5 ml PBS and pipetted dropwise into 5 ml of 1% buffered paraformaldehyde on ice with gentle mechanical mixing. After 15 min incubation on ice, cells were pelleted, washed with 10 ml cold PBS, and the pellets were resuspended in 1 ml 70& ethanol pre-cooled at −20° C. Samples stored at −20° C. overnight were resuspended, divided into two equal aliquots, collected by centrifugation, and washed twice with ice cold PBS. Duplicate samples were resuspended in 50 μl reaction mixtures containing 1× terminal deoxynucleotidyl transferase (TdT) buffer, $CoCl_2$, and digoxigenin-11-UTP with or without 0.5 μl TdT (all supplied as a TdT kit by Boehringer Mannheim Corp., Indianapolis, Ill.). After 30 min incubation at 37° C., 1 ml of ice cold PBS was added, and recentrifuged cells were suspended in 100 μl of a 1:40 dilution in PBS of anti-digoxigenin-FITC monoclonal antibody and incubated for 30 minutes in the dark at room temperature. Cells were sequentially washed in 1 ml of ice cold PBS containing 2mM sodium azide and 0.35% bovine serum albumin (BSA), and then in 1 ml 0.1% Triton X-100 in PBS, and resuspended in 1 ml PBS-azide-BSA containing 50 μg/ml propidum iodide. RNAse (50 μg/ml) was added, and after 30 minute incubation at room temperature, samples were filtered for flow cytometry and analyzed for DNA content (red PI fluorescence) and TdT-labeled DNA fragments (green FITC) on a Becton Dickinson FACScan (Matsushime et al., 1991). DNA fragmentation was quantitated by determining the difference in FITC fluorescence between duplicate samples incubated with and without TdT. Human Jurkat T cells treated with 100 μM etoposide for 6 hrs were routinely included as positive controls for cells undergoing apoptosis.

Immunofluorescence

Cells were harvested 48 hours after infection and spun onto glass slides ($5\times10^4$ cells/slide) using a Scimetrics Cytospin3 at 500 rpm for 5 min. Following fixation for 10 min at room temp in 3% paraformaldehyde, slides were washed 3 times with phosphate-buffered saline (PBS), permeabilized in 0.2% Triton X-100 for 10 min at room temperature, and washed 3 more times with PBS. After 30 min incubation in blocking solution (PBS containing 1% dry milk), cells were incubated at room temperature in a humidified chamber for 1 hour with primary antibody (5 μg/ml 12CAS MAb or 1:600 ARF-p19 polyclonal antiserum diluted in blocking solution). To confirm the specificity of ARF-p19 antiserum, primary antibody was incubated with ARF-p19 peptide for 1 hour at temperature prior to incubation with cells. After six washes with blocking solution, secondary antibody incubations were performed in blocking solution for 30 min, using 1:50 dilutions of either FITC-conjugated sheep anti-mouse or FITC conjugated donkey anti-rabbit IgG (Amersham, Arlington Heights, Ill.). After six washes with PBS, cells were stained with Hoescht dye 33258 (1 μg/ml), wet mounted with vectashield medium (Vector, Burlingame, Calif.), and photographed at 600X magnification through a microscope equipped with epifluorescence optic (Olympus, Lake Success, N.Y.).

When cytospins were prepared from cells harvested 48 hours after infection with viruses encoding HA-tagged ARF-p19, immunofluorescence performed with antibodies to the ARF-p19 C-terminus (FIG. 5(A)) or to the N-terminal HA epitope (FIG. 5(C)) revealed the protein in the cell nucleus. Greater than 80% of the infected cells stained brightly compared to uninfected cells (not shown) or to those stained with peptide blocked serum (FIG. 5(B)). No nuclear dissolution or mitotic figures were observed, confirming that the cells arrested in interphase.

Example 6
Effects of ARF-p19 on CDK Activity

When lysates of ARF-p19-infected NIH-3T3 cells were precipitated with specific antisera to CDC2 or CDK2 and histone H1 kinase activity was measured in immune complexes, the activities of both CDKs were greatly reduced relative to proliferating populations infected with the control vector (data not shown). The observed ~10-fold decrease in CDC2 kinase is consistent with the loss of the mitotic fraction, whereas the ~5 fold drop in CDK2 activity likely reflects a redistribution of cells from S phase into G1 and G2. Indeed, given the dissimilarity in structure between ARF-p19 and known CDK inhibitors, it seems unlikely that the protein interacts directly with CDKs or cyclins. In agreement, when CDC2, CDK2, CDK4, CDK6, cyclins D1, D2, E, and A immunoprecipitates from NML cell lysates were blotted with anti-ARF-p19, no coprecipitation of ARF-p19 was observed. Reconstruction experiments with baculovirus expression vectors in insect Sf9 cells also failed to provide convincing evidence for associations between ARF-p19 and these cell cycle regulators. The mechanism(s) by which ARF-p19 induces cell cycle arrest remains unclear, although the propensity of some cells to arrest in G2 argues that these ARF-p19-induced effects are pRb-independent.

Example 7
ARF-p19 Mutations in Human Cancers

Current evidence indicates that InK4a-p16 functions upstream of cyclin D-dependent kinases and pRb in a biochemical pathway that regulates exit of G1 phase cells into S phase. InK4a-p16 cannot induce G1 arrest in cells that lack pRb function (Guan et al., Genes Devel. 8:2932–2952 (1994); Tam et al., Oncogene 9:2663–2674 (1994); Lukas et al., Nature 375:503–506 (1995); Medema et al., Proc. Natl. Acad. Sci. USA 92:6289–6293 (1995); Koh et al., Nature 375:506–510 (1995)), and in lung cancer, INK4A deletions are restricted to tumors that retain pRb activity and vice versa, implying that a loss of either gene makes compromise of the other irrelevant (Otterson et al., Oncogene 9:3375–3378 (1994)). Increased levels of InK4a-p16 are generally observed in pRb-negative tumor cells (Serrano et al., Nature 366:704–707 (1993); Bates et al., Oncogene 9:1633–1640 (1994); Lukas et al., J. Cell. Biol. 125:625–638 (1994); Tam et al., Oncogene 9:2663–2674 (1994)), suggesting that InK4a-p16 expression may be somehow governed by pRb itself or, alternatively, that pRb provides a predisposing selective pressure that favors elimination of pRb-mediated controls (Sherr and Roberts, Genes Devel. 9:1149–1163 (1995)).

Of the numerous InK4a-p16 mutations found in human cancers, only a few have been experimentally evaluated for effects on the cell cycle. However, two which clearly abrogate InK4a-p16 inhibitory functions (R87β and H98β in Koh et al., Nature 375:506–510 (1995)) are silent with regard to ARF-p19, and another (P114L in Lukas et al., Nature 375:503–506 (1995)) falls outside the region of overlap between InK4a-p16 and ARF-p19, indicating that the latter is not a target of inactivating mutations in these cases.

Nevertheless, most mutations involving INK4A in cancer cells fall within the 5' half of exon 2, raising the possibility that some may dually affect InK4a-p16 and ARF-p19 or, conceivably, ARF-p19 alone. About 60% of mutations in InK4a-p16 cluster within the region overlapping ARF-p19 (Hirama and Koeffler, Blood 86:841–854 (1995)), and more than 80% of these affect ARF-p19 primary structure. FIG. 6 shows the predicted ARF-p19 mutations within this segment, compiled from data obtained with primary tumors, xenografts, and established cell lines (Kamb, A. et al., Science 264:436440 (1994a), Nature Genet 8:22–26 (1994b); Caldas et al., Nature Genet. 8:27–32 (1994); Hussussian et al., *Nature Genet.* 8:15–21 (1994); Ohta et al., *Cancer Res* 54:5269–5272 (1994); Zhang et al., *Cancer Res* 54:5050–5053 (1994); Mori et al., *Cancer Res.* 54:3396–3397 (1994); Hayashi et al., *Biochem. Biophys. Res. Commun.* 202:1426–1430 (1994)). Of 50 missense and frame shift mutations, 39 involve codons conserved between human and mouse ARF-p19 (residues in bold type) and four (marked by asterisks) are silent in InK4a-p16. The most frequently mutated ARF-p19 residues in sporadic cancers are Gly-69, Pro-94, Arg-98, each of which is conserved in humans and mice, and the most common disease-related alteration in melanoma kindreds (Hussussian et al., *Nature Genet.* 8:15–21 (1994); Kainb et al., *Nature Genet.* 8:22–26 (1994b)) converts conserved Arg-115 of ARF-p19 to Leu. A further complication is that frame shift mutations have the potential to produce chimeric proteins. For example, those involving ARF-p19 Gln-70 (Hayashi et al., *Biochem. Biophys. Res Commun.* 202:1426–1430 (1994)) and Gly-74 (Ohta et al., *Cancer Res.* 54:5269–5272 (1994)) should result in INK4Aα transcripts encoding InK4a-p16/ARF-p19 fusions in which the majority of exon-2 sequences encode ARF-p19 residues. Conversely, an ARF-p19 frame shift involving Gly-102 (Hayashi et al., *Biochem. Biophys. Res Commun.* 202:1426–1430 (1994)) would yield a β transcript encoding the C-terminal half of InK4a-p16. To the extent that mutations in ARF-p19 contribute to aberrant growth control and tumorigenesis, detection and analysis of ARF-p19-specific nucleic acids (Example 2) in a mammal serves to diagnose, or assist in the diagnosis of, existing tumors in the mammal, or to predict the mammal's predisposition for developing certain forms of cancer.

What is claimed is:

1. An isolated antibody that binds to an ARF-p19 polypeptide, wherein said ARF-p19 polypeptide is a human ARF-p19 polypeptide comprising the amino acid sequence of SEQ ID NO:4.

2. The isolated antibody of claim 1, wherein the antibody is generated with an immunoreactive peptide derived from SEQ ID NO:4.

3. The isolated antibody of claim 2, wherein the antibody is generated with a peptide comprising 5 to 100 contiguous amino acids of SEQ ID NO:4.

4. The isolated antibody of claim 3, wherein the immunoreactive peptide is prepared by organic synthesis.

5. The isolated antibody of claim 2, wherein the antibody is generated with a fusion peptide comprising 5 to 100 contiguous amino acids of SEQ ID NO:4.

6. The isolated antibody of claim 3, wherein the antibody is generated with a peptide comprising 5 contiguous amino acids of amino acid residues 1 to 65 of SEQ ID NO:4.

7. The isolated antibody of claim 1 which is labeled.

8. The isolated antibody of claim 1 which is a monoclonal antibody.

9. The isolated antibody of claim 1 which is a polyclonal antibody.

10. The isolated antibody of claim 3, wherein said peptide is conjugated to a carrier.

* * * * *